(12) United States Patent
Matsumoto et al.

(10) Patent No.: US 6,494,827 B1
(45) Date of Patent: Dec. 17, 2002

(54) ENDOSCOPE DEVICE AND OPERATION APPARATUS

(75) Inventors: Kazutaka Matsumoto, Fuchu (JP); Hiroyuki Sangu, Hino (JP); Itaru Osaki, Yokohama (JP); Masakazu Gotanda, Kanagawa (JP); Seiichi Hosoda, Hino (JP); Shinji Hatta, Hachioji (JP); Akira Shiga, Hidaka (JP); Katsushi Watanabe, Hachioji (JP); Koji Yasunaga, Hino (JP); Hiroshi Takahashi, Hachioji (JP); Masaru Karasawa, Yokohama (JP); Takeaki Nakamura, Hino (JP)

(73) Assignee: Olympus Optical Co., Ltd. (JP)

( * ) Notice: Subject to any disclaimer, the term of this patent is extended or adjusted under 35 U.S.C. 154(b) by 0 days.

(21) Appl. No.: 09/428,349

(22) Filed: Oct. 27, 1999

(30) Foreign Application Priority Data

| Oct. 29, 1998 | (JP) | ........................................... | 10-308856 |
| Jan. 20, 1999 | (JP) | ........................................... | 11-012177 |
| Sep. 7, 1999 | (JP) | ........................................... | 11-253330 |
| Sep. 9, 1999 | (JP) | ........................................... | 11-256292 |

(51) Int. Cl.[7] .................................................. A61B 1/06
(52) U.S. Cl. ........................ 600/118; 600/117; 600/178
(58) Field of Search ................................ 600/117, 118, 600/178, 179, 180; 340/636; 324/435; 429/90–93; 362/317

(56) References Cited

U.S. PATENT DOCUMENTS

| 4,355,275 A | * | 10/1982 | Anglin .......................... 307/38 |
| 5,510,205 A | * | 4/1996 | Ozer ............................ 429/91 |
| 5,588,950 A | | 12/1996 | Sano et al. |
| 5,602,459 A | * | 2/1997 | Rogers ......................... 320/134 |
| 5,623,194 A | * | 4/1997 | Boll et al. .................... 320/137 |
| 5,656,919 A | * | 8/1997 | Proctor et al. ................. 429/90 |
| 5,721,987 A | * | 2/1998 | Ozawa ......................... 396/263 |
| 5,994,791 A | * | 11/1999 | Rayner ......................... 307/31 |
| 6,004,264 A | * | 12/1999 | Sano et al. ................... 600/178 |
| 6,064,182 A | * | 5/2000 | Eguchi ......................... 429/91 |
| 6,078,871 A | * | 6/2000 | Anderson ..................... 320/128 |
| 6,135,947 A | * | 10/2000 | Watanabe et al. ............ 600/178 |
| 6,174,617 B1 | * | 1/2001 | Hiratsuka et al. ............. 429/90 |
| 6,184,794 B1 | * | 2/2001 | Tucholski ..................... 429/93 |
| 6,202,642 B1 | * | 3/2001 | McKinnon et al. ..... 128/200.23 |
| 6,239,787 B1 | * | 5/2001 | Sugaya ........................ 345/169 |
| 6,252,511 B1 | * | 6/2001 | Mondshine et al. ......... 340/636 |

FOREIGN PATENT DOCUMENTS

| JP | 2-43501 | 9/1990 |
| JP | 10-43133 | 2/1998 |

* cited by examiner

Primary Examiner—John P. Leubecker
(74) Attorney, Agent, or Firm—Ostrolenk, Faber, Gerb & Soffen, LLP

(57) ABSTRACT

An endoscope apparatus capable of preventing occurrence of problems trouble attributable to exhaustion of a battery has an endoscope and a battery-powered light source. The endoscope has a light guide fiber bundle over which illumination light is propagated. The battery-powered light source is freely detachably attached to the endoscope, and includes an illumination lamp and a battery. The illumination lamp supplies illumination light to the incidence end of the light guide fiber bundle on which illumination light falls. The battery serves as a power supply causing the illumination lamp to light. At least one of the endoscope and battery-powered light source has an indication unit for notifying a user of the amount of electrical energy contained in the battery.

20 Claims, 30 Drawing Sheets

ENDOSCOPE DEVICE AND OPERATION APPARATUS

BACKGROUND OF THE INVENTION

1. Field of the Invention

The present invention relates to an endoscope device and an operation apparatus having a battery as a power supply.

2. Description of the Related Art

In the past, a type of endoscopic light source unit having a lamp illuminated by utilizing power supplied from an outlet included in an endoscope apparatus.

By contrast, for example, Japanese Unexamined Patent Publication No. 10-43133 has proposed an endoscope to which a battery-powered light source is freely detachably attached. The battery-powered light source utilizes a battery as a power supply.

Endoscope apparatuses having a compact battery-powered light source attached to an endoscope are superior in portability and usable in places where a power supply is unavailable. This type of endoscope apparatus proves very effective when applied to usage in places where it is hard to carry a large light source apparatus that needs a power supply.

However, the battery-powered light source uses a battery, which may be a dry cell or rechargeable battery, as a power supply. If the remaining amount of electrical energy contained in the battery is unknown the battery may be exhausted on an unexpected occasion. This leads to a possibility that an examination may have to be suspended, that the endoscope apparatus may fail to meet an emergency situation, or that the excellent features of the endoscope apparatus may not be exerted fully.

Moreover, a power switch of a dialed or pushed type may be formed on the battery-powered light source in order to turn on or off the lamp. In this case, the on or off state of the power switch is discerned from the appearance of the switch or the positional relationship between an indication inscribed near the switch and the switch. When the power switch is formed at the end or side of the light source opposite to a user's face, it is hard to discern the on or off state. The battery may be exhausted because the user forgot to turn off the switch.

In recent years, an electric ultrasonic operation apparatus to be used in combination with an optical viewer has been widely adopted as a means to be inserted into an abdominal cavity or articular cavity for observing and treating a lesion. Moreover, an electric cautery or ultrasonic operation apparatus has been widely used as an operation apparatus that is not of a type being used trans-endoscopically.

For example, Japanese Examined Patent Publication No. 2-43501 describes an intracavity resection apparatus having a treatment drill thereof inserted into a trocar and cannula for piercing the wall of a body cavity. Herein, an optical viewer is freely removably inserted into a channel lying through a drill instrument. A drill shaft having an umbrella cutting blade attached to the tip thereof and a flexible drive shaft are included in an insertion shaft of the drill instrument. The insertion shaft can be rotated using a driving motor. The driving motor is driven using a battery incorporated in a hand-held control section of the drill instrument.

However, the battery that is rather heavy is incorporated in the hand-held control section of the intracavity resection apparatus. This results in a heavy operation apparatus. When it takes much time to complete surgery, an operator must incur a great load. It is therefore hard to conduct surgery with high precision or for a long period of time.

SUMMARY OF THE INVENTION

The present invention provide an endoscope device and an operation apparatus enabling a user to recognize an amount of electrical energy contained in a battery.

The present invention also provides an endoscope device and an operation apparatus making it easy to discern an amount of electrical energy remaining in a battery during use.

The present invention also provides an endoscope device and an operation apparatus capable of preventing unexpected exhaustion of a battery attributable to the fact that a user forgot to check the state of the battery.

Still further the present invention provides an endoscope device capable of indicating an amount of electrical energy remaining in a battery even with an endoscope detached, and making it easy to check the amount of electrical energy remaining in the battery.

In addition the present invention provides an endoscope device and an operation apparatus having a portion thereof to be held for performing manipulations lightened in weight and thus offering improved maneuverability.

Briefly, an endoscope device in accordance with the present invention consists of an endoscope having a light guide fiber bundle over which illumination light is propagated, and a battery-powered light source including an illumination lamp and a battery. The illumination lamp is freely detachably attached to the endoscope and supplies illumination light to one end of the light guide fiber bundle on which illumination light is incident. The battery serves as a power supply for lighting the illumination lamp.

At least one of the endoscope and battery-powered light source has an indication means to indicate the amount of electrical energy contained in a battery. The indication means includes an electrical battery energy detecting means for detecting an amount of electrical energy contained in the battery, and a capacity-of-battery reporting means for reporting the amount of electrical energy contained in the battery to a user. Consequently, the endoscope device can prevent occurrence of a problem attributable to exhaustion of a battery.

An operation apparatus having a battery as a power supply has a surgical instrument and a battery housing. The surgical instrument consists of an insertion shaft to be inserted into a body cavity, a control section united with the back end of the shaft, and a cure device attached to the tip of the insertion shaft and used to perform resection, coagulation, or any other cure. A drive unit for driving the cure device is incorporated in the control section. The battery housing accommodates a battery for supplying power to the drive unit. The drive unit incorporated in the surgical instrument and the battery housing are linked by a flexible cord. This results in the operation apparatus having the surgical instrument of excellent maneuverability.

BRIEF DESCRIPTION OF THE DRAWINGS

FIG. 1 shows the appearance of an endoscope apparatus including an endoscope and a battery-powered light source having a liquid crystal monitor for indicating the remaining charge of a battery;

FIG. 2 is an explanatory diagram concerning the structures of portions of the battery-powered light source and endoscope which are detachably attached to each other;

FIG. 3 is an explanatory diagram concerning the components of the endoscope apparatus;

FIG. 4 is an explanatory diagram concerning the on-off operation of the battery-powered light source;

FIG. 5 is a block diagram for explaining a light source operation circuit incorporated in the battery-powered light source;

FIG. 6 is an explanatory diagram concerning the positional relationship between the battery-powered light source that is turned on and an eyepiece unit;

FIG. 9 is an explanatory diagram concerning an endoscope apparatus consisting of an endoscope having an indication unit, which is used to report the capacity of a battery, included in an eyepiece unit, and a battery-powered light source;

FIG. 10 is an explanatory diagram concerning the indication unit formed on the perimeter of an observation window of the eyepiece unit;

FIG. 18 is an explanatory diagram concerning a light source operation circuit;

FIG. 19 is a flowchart describing a program of indicating an amount of electrical energy remaining in a battery;

FIG. 20 is a graph showing a discharge characteristic curve concerning a battery;

FIG. 21 is an explanatory diagram concerning a light source operation circuit;

FIG. 22 is a flowchart describing a program of indicating an amount of electrical energy remaining in a battery;

FIG. 23 is a block diagram for explaining a light source operation circuit;

FIG. 24 shows an example of different indications appearing on a liquid crystal panel;

FIG. 25 is a graph showing a discharge characteristic curve concerning a typical battery;

FIG. 26 shows the circuitry for checking the state of a battery;

FIG. 27 is an explanatory diagram concerning the relationship between a discharge characteristic and an indicating action;

FIG. 28 is an explanatory diagram showing the overall configuration of an ultrasonic operation apparatus;

FIG. 29 shows the configuration of an electric system;

FIG. 37 shows an ultrasonic cure device having the capability of a life meter; and FIG. 38 is an explanatory diagram concerning actions of the life meter.

DESCRIPTION OF THE PREFERRED EMBODIMENTS

Embodiments of the present invention will be described with reference to the drawings.

The first embodiment of the present invention will be described with reference to FIG. 1 to FIG. 6.

Figure 1:
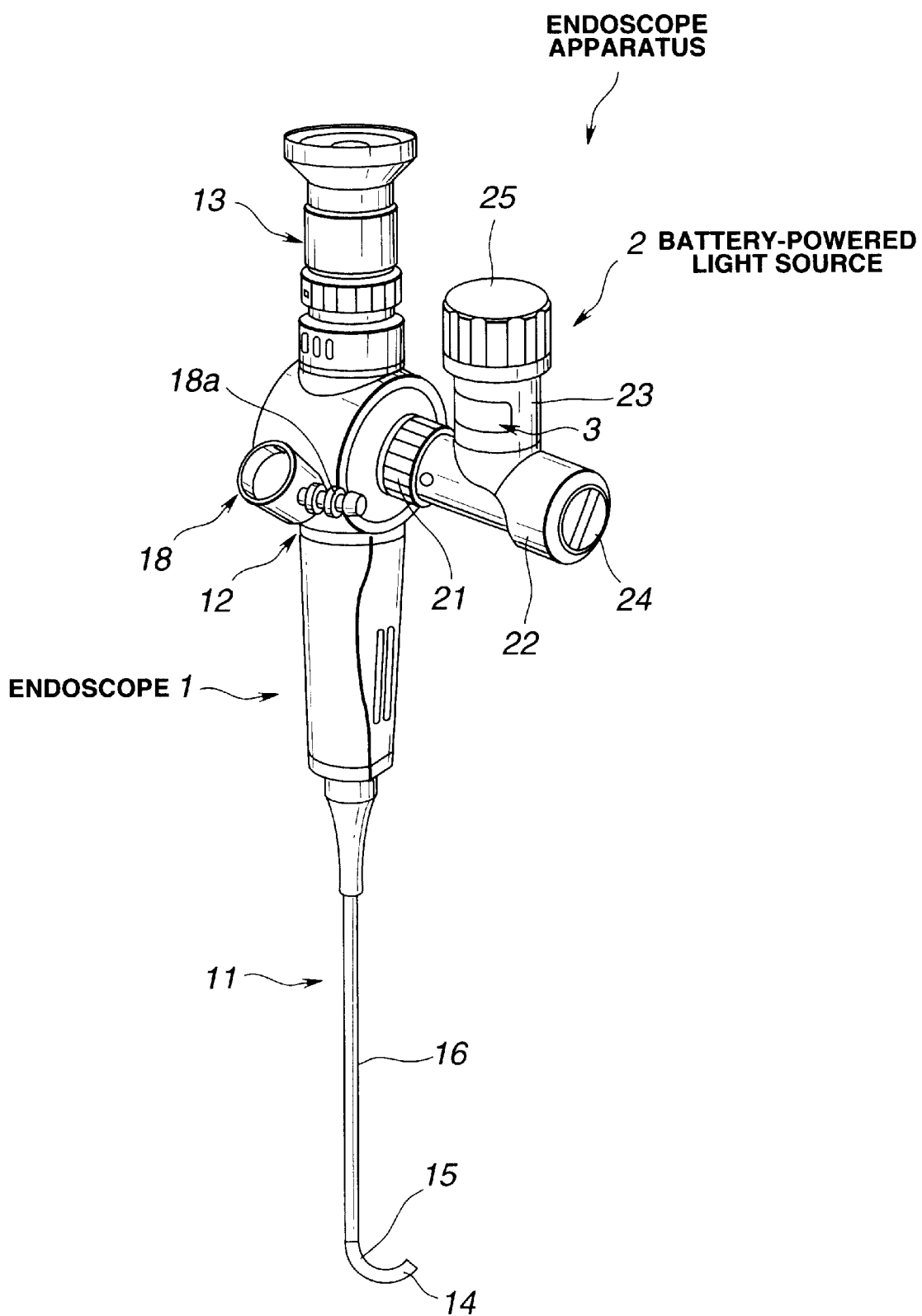
FIG. 1 to FIG. 6 show the first embodiment of the present invention.

To begin with, an endoscope apparatus of the present embodiment will be described with reference to FIG. 1 to FIG. 3. As shown in FIG. 1, the endoscope apparatus consists of an optical endoscope 1 for use in observing, for example, the internal cavity of a human body. A battery-powered light source 2 is a compact light source unit freely detachably attached to the endoscope 1. A liquid crystal panel 3 serving as a capacity-of-battery reporting means included in an indication means to indicate the remaining capacity of a battery is included in the battery-powered light source 2.

The endoscope 1 consists of an insertion portion 11 having flexibility, a control section 12 located at the proximal end of the insertion portion 11, and an eyepiece unit 13 located at the proximal end of the control section 12.

The insertion portion 11 has a rigid distal portion 14, a bending section 15, and a flexible tube 16 arranged in that order from the distal end thereof. The bending section 15 that is freely bendable communicates with the proximal end of the distal portion 14. The flexible tube 16 that has flexibility communicates with the proximal end of the bending section 15. The bending section 15 can be angled in a desired direction by manipulating a knob 19 (FIG. 6) formed on the control section 12.

Figure 2:
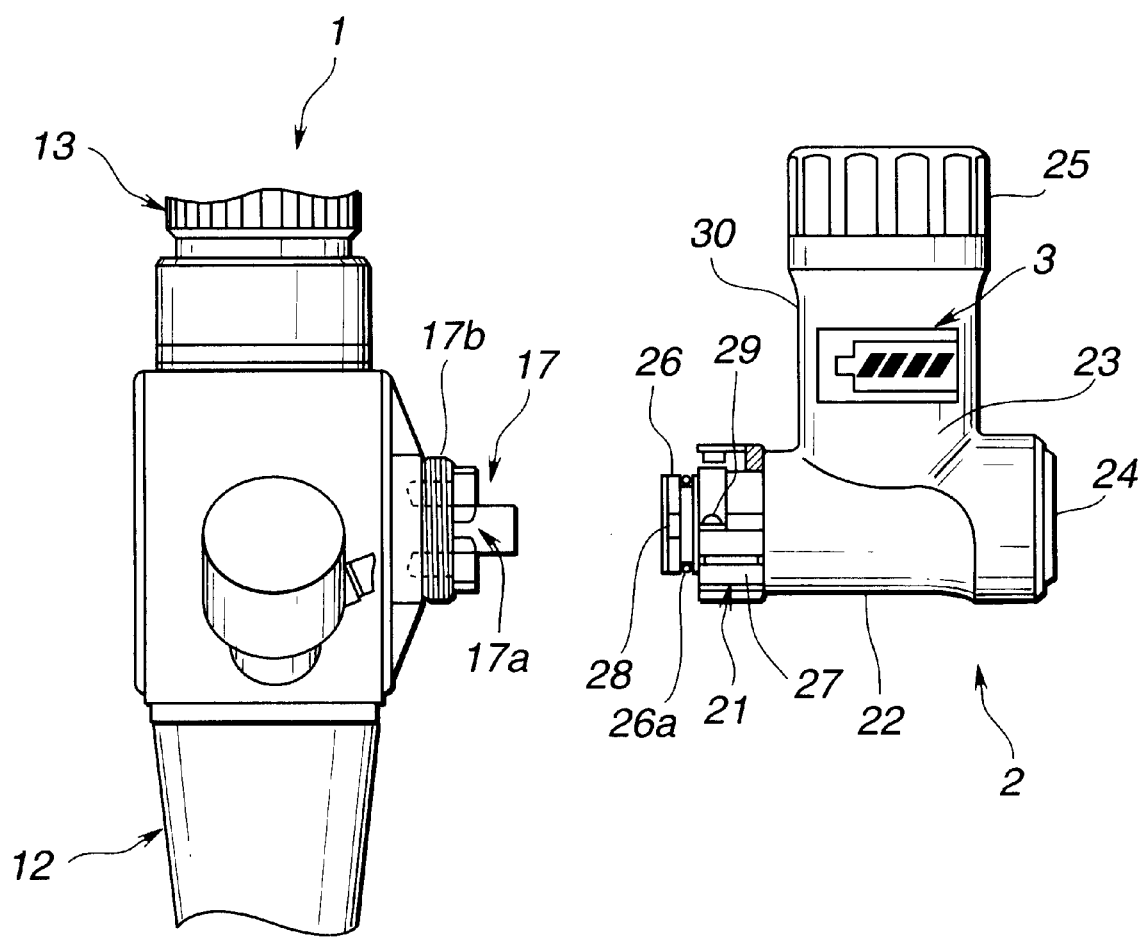
Figure 3:
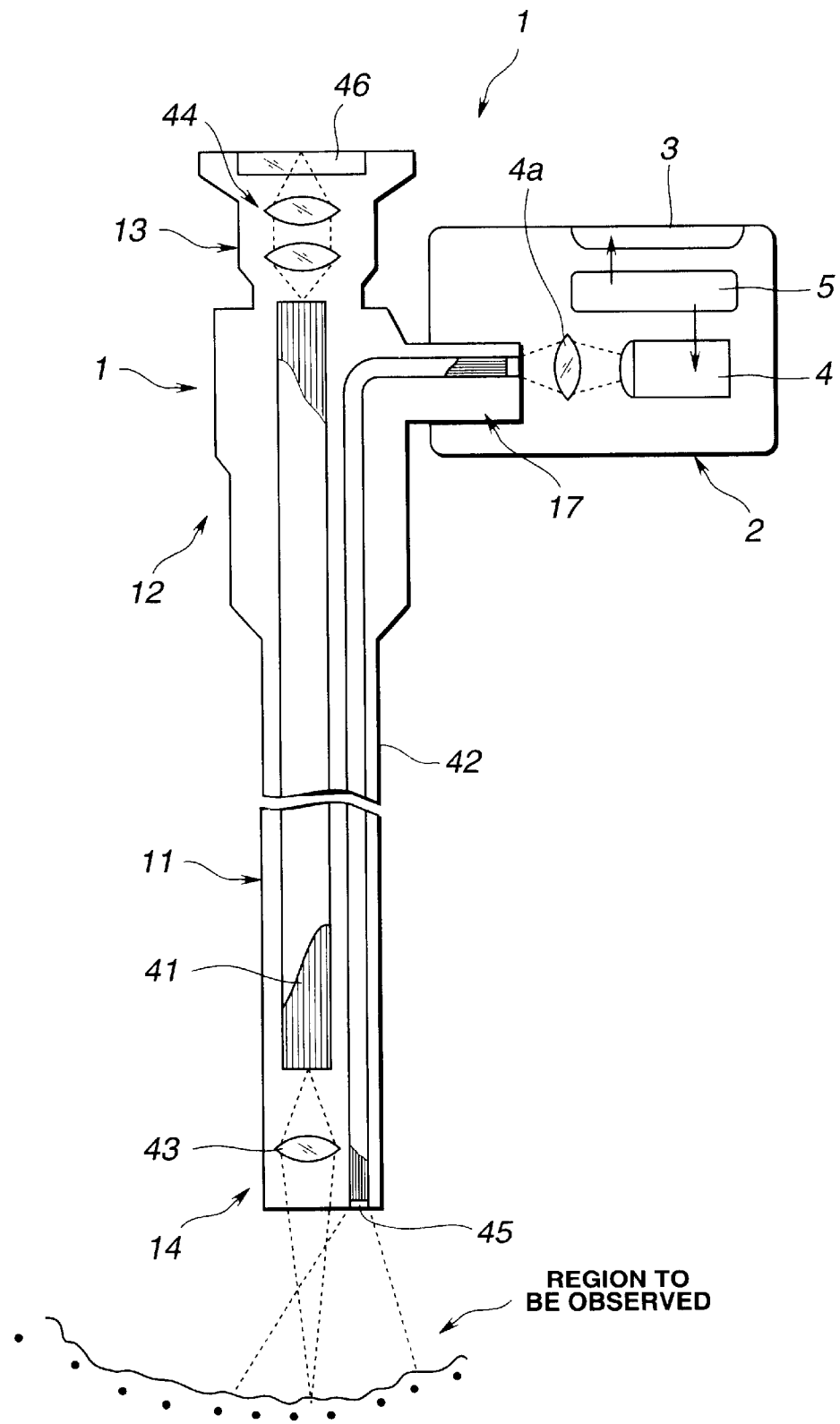

On the other hand, as shown in FIG. 1 to FIG. 3, the battery-powered light source 2 consists of an attachment portion 21, a lamp stowage portion 22, and a battery stowage portion 23. The attachment portion 21 is a coupling portion to be coupled to the control section 12. An illumination lamp 4 for supplying illumination light is stowed in the lamp stowage portion 22. A battery 5, that is, one or a plurality of dry batteries or a chargeable battery, is stowed in the battery stowage portion 23.

A lamp cap 24 is freely detachably attached to the proximal end of the lamp stowage portion 22. Moreover, a battery cap 25 is freely detachably attached to the proximal end of the battery stowage portion 23. The lamp 4 or battery 5 can be replaced with a new one by detaching the cap 24 or 25.

As shown in FIG. 3, an image guide fiber bundle 41 and a light guide fiber bundle 42 are passed through the insertion portion 11. A view image is propagated over the image guide fiber bundle 41, and illumination light emanating from the battery-powered light source 2 is transmitted over the light guide fiber bundle 42. Moreover, a suction channel that is not shown is passed through the insertion portion 11.

The distal part of the image guide fiber bundle 41 is secured together with an objective lens 43 in the distal portion 14. The proximal part of the image guide fiber bundle 41 is secured at a position at which an eyepiece 44 incorporated in the eyepiece unit 13 forms an image.

On the other hand, the distal part of the light guide fiber bundle 42 is secured together with an illumination window 45 in the distal portion 14. The proximal part of the light guide fiber bundle 42 is secured in a light guide base 17 so that the incidence end of the light guide fiber bundle on which illumination light falls will be opposed to the illumination lamp 4 stowed in the lamp stowage portion 22.

Illumination light emanating from the illumination lamp 4 is converged on the incidence end of the light guide fiber bundle 42, on which illumination light falls, by means of a condenser 4a. Thereafter, the illumination light is propagated over the light guide fiber bundle 42, and then irradiated to a region to be observed.

The distal part of the suction channel is secured in the distal portion 14. The suction channel is used as a treatment channel through which an endoscopic forceps that is not shown is passed by way of a channel port 18. A suction port 18a communicates with the channel port 18. An observation window 46 is looked through for observing a region.

As shown in FIG. 2, the attachment portion 21 of the battery-powered light source 2 includes an attachment body 26, a locking member 27, an index 28, and a positioning pin 29. The attachment body 26 is fitted in the light guide base 17. The locking member 27 is mounted on the attachment body 26 so that it can rotate freely. A female screw is threaded on the inner circumference of the locking member 27. The index 28 for indicating a specified position is located on the outer circumference of the attachment body 26. The positioning pin 29 is positioned with the index 28 as a reference.

The liquid crystal panel 3 displaying an indicator 30 is located on the side surface of the battery stowage portion 23. The indicator 30 is a graphic simulating a battery and used to indicate the capacity of the battery as an index so that an amount of electrical energy contained in the battery 5 can be discerned at sight.

The light guide base 17 of the control section 12 of the endoscope 1 has a pin receptor portion 17a and a male screw portion 17b. The positioning pin 29 is fitted into the pin receptor portion 17a. The male screw portion 17b is meshed with the female screw threaded on the locking member 27. Moreover, the battery-powered light source 2 can be swiveled on the control section 12 with the attachment body 26 united with the control section 12 as an axis of rotation. This is intended to make it possible to light or put out the lamp 4.

The positioning pin 29 is fitted in the pin receptor portion 17a of the light guide base 17, and the female screw threaded on the locking member 27 is meshed with the male screw portion 17b. Consequently, the battery-powered light source 2 is, as shown in FIG. 1, united with and fixed to the control section 12 of the endoscope 1. A this time, a watertight ring 26a mounted on the attachment body 26 comes into close contact with the inner circumference of the light guide base 17 having the male screw portion 17b. The joint of the light guide base and attachment body is thus held watertight. Moreover, backlash or looseness between coupled portions can be prevented.

In the coupled state shown in FIG. 1, the lamp 4 is off. According to the present embodiment, the battery-powered light source 2 is swiveled from the position indicated with a dashed line in FIG. 4 to the position indicated with a solid line in order to light the lamp 4. Incidentally, the battery-powered light source shown in FIG. 1 lies at the position indicated with the dashed line in FIG. 4. At this time, the liquid crystal panel 3 is opposed to a user's face by the side of the eyepiece unit 13. A user can therefore view the liquid crystal panel 3 with his/her eye having approached the eyepiece unit 13, and discern an amount of electrical energy contained in the battery 5.

Figure 5:
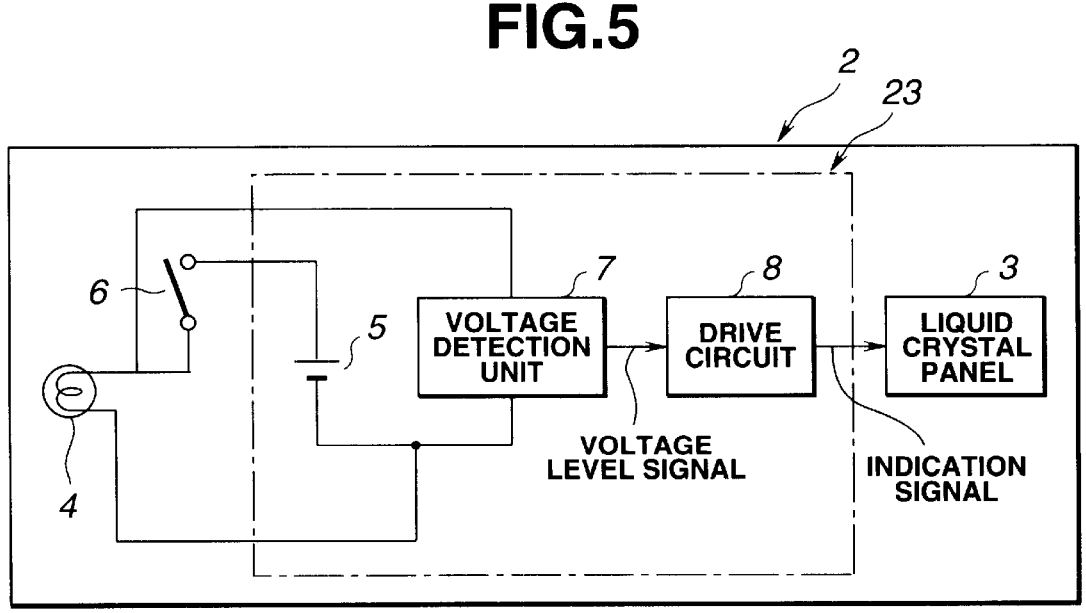

Referring to FIG. 5, a light source operation circuit included in the battery-powered light source 2 will be described.

As illustrated, the battery-powered light source 2 includes the lamp 4, the battery 5, a switch 6, a voltage detection unit 7, a drive circuit 8, and the liquid crystal panel 3. The lamp 4 emanates illumination light. The battery 5 supplies power to the lamp 4. The switch 6 is located at the middle of a conducting path linking the lamp 4 and battery 5. The switch 6 is turned on or off along with a swiveling movement to be made for changing the conducting path from a conducting state to a nonconducting state or vice versa. The voltage detection unit 7 is an electrical battery energy detecting means for detecting a voltage given by the battery 5 and producing a voltage value signal. The drive circuit 8 produces a driving signal according to the voltage value signal output from the voltage detection unit 7. The liquid crystal panel 3 notifies a user of the amount of electrical energy contained in the battery 5 in response to the driving signal output from the drive circuit 8.

One or a plurality of comparison circuits for comparing the value of a detected voltage with the value of a reference voltage designed to be given by the battery, and producing a voltage value signal is incorporated in the voltage detection unit 7. The voltage value signal indicates stepwise an amount of electrical energy contained in the battery. A processing circuit for arithmetically producing a driving signal from the voltage value signal is incorporated in the drive circuit 8.

According to the present embodiment, the indicator 30 simulating a battery is, as shown in FIG. 2, displayed on the liquid crystal panel 3. The color of the indicator 30 is lightened in four steps, whereby the amount of electrical energy contained in the battery 5 is discernible. The drawing shows a fully-charged state out of four stepwise states.

The drive circuit 8 and liquid crystal panel 3 are electrically connected to the battery 5. Moreover, the number of comparison circuits included in the voltage detection unit 7 corresponds to the number of stepwise states indicated by the indicator 30. Furthermore, the number of indicated stepwise states is not limited to four but may be larger or smaller.

Now, operations to be performed by the endoscope apparatus will be described.

To begin with, the battery-powered light source 2 is coupled and fixed to the endoscope 1 in order to constitute the endoscope apparatus.

Figure 4:
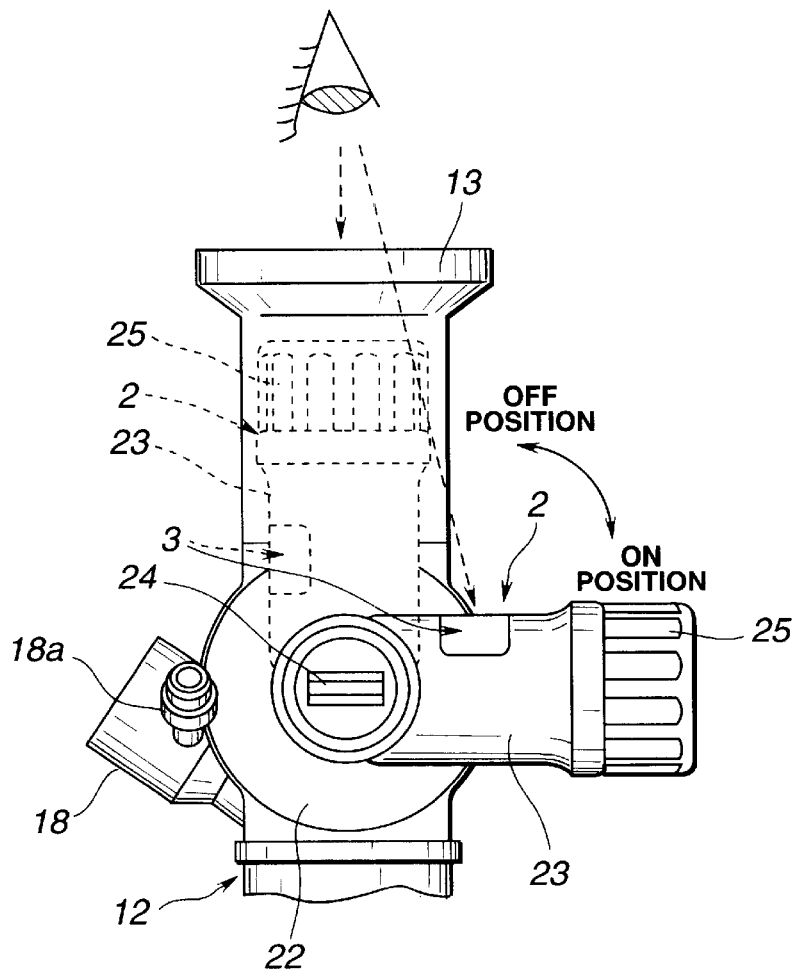
Figure 6:
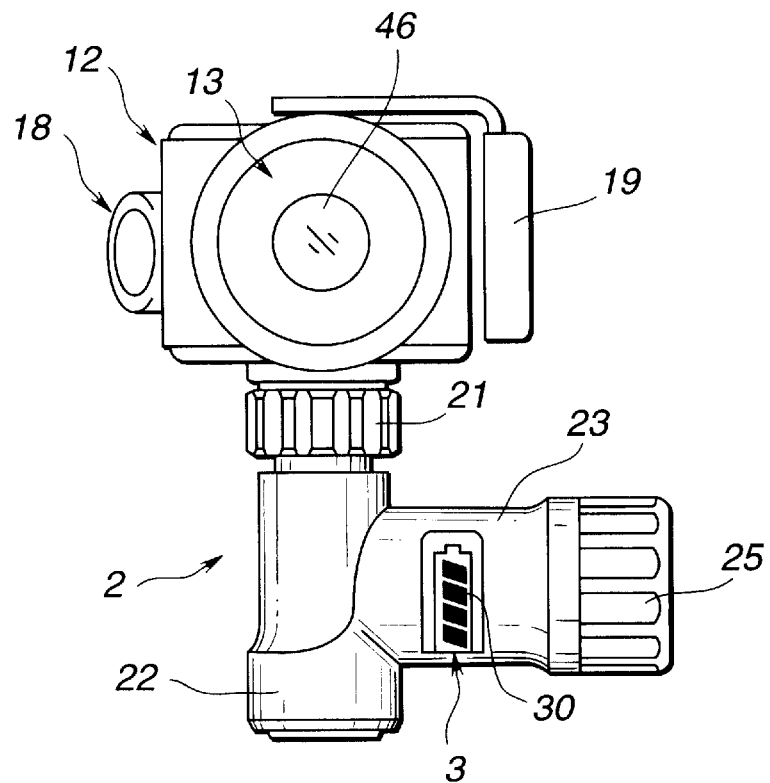

Thereafter, the battery-powered light source 2 is, as shown in FIG. 4 and FIG. 6, swiveled substantially 90° on the control section 12 with the attachment body 26 united with the control section 12 as an axis of rotation. The power switch 6 is thus turned on and the lamp 4 is lit. At this time, the display surface of the liquid crystal panel 3 and the observation window 46 of the eyepiece unit 13 are oriented in the same direction. When an operator advances his/her face to the eyepiece unit 13 for endoscopic observation, he/she will confront the liquid crystal panel 3.

Moreover, when the lamp 4 is illuminated, the comparison circuits in the voltage detection unit 7 each compare the value of a detected voltage with the value of a reference voltage designed to be given by the battery 5. Based on the results of the comparison, the voltage detection unit 7 produces a voltage value signal and outputs it to the drive circuit 8. In response to the voltage value signal, the drive circuit 8 arithmetically processes the voltage value signal and produces a driving signal. The driving signal is output to the liquid crystal panel 3.

According to the received driving signal, the liquid crystal panel 3 indicates the amount of electrical energy contained in the battery 5 in the form of the indicator 30 simulating a battery. A user discerns the indicator 30 and judges whether it is necessary to replace the battery with a new one or prepare an auxiliary battery. The user can thus keep using the endoscope apparatus 1.

As mentioned above, the indicator for informing a user of an amount of electrical energy contained in a battery included in the battery-powered light source is displayed on the liquid crystal panel included in the battery-powered light source. The user can judge the remaining amount of electrical energy contained in the battery on sighting the indicator. It can therefore be prevented that the user keeps using the endoscope apparatus while being unaware of the fact that the remaining capacity of the battery is insufficient.

Moreover, when the battery-powered light source is conducting, the indicator indicating a charged state of a battery is displayed on the liquid crystal panel. By checking if the indicator is displayed, a user can judge whether the battery-powered light source is conducting. The user can therefore readily judge whether the battery-powered light source is conducting.

Furthermore, the liquid crystal panel is located at a position where it can be discerned readily by an operator during endoscopic observation. The operator can therefore readily check an amount of energy remaining in a battery prior to use. Moreover, the operator can readily check the amount of energy contained in the battery during observation.

Consequently, the problem is avoided that a battery is exhausted unexpectedly due to a failure to check an amount of energy remaining in the battery.

A switch or timer that is not shown may be installed on a stage preceding the voltage detection unit 7. The voltage detection unit 7 may be driven to conduction at any time or cyclically so that it will detect the level of a voltage given by the battery 5. Thus, the voltage detection unit 7 can detect a voltage according to any timing or cyclically. This leads to limited consumption of the battery.

Moreover, instead of incorporating the comparison circuits in the voltage detection unit 7, an A/D converter may be used to indicate an amount of electrical energy contained in a battery in the form of numerals on the liquid crystal panel 3.

Figure 7:
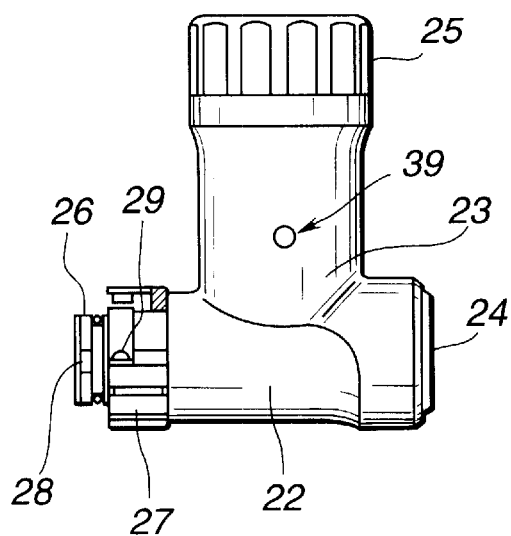
FIG. 7 is an explanatory diagram concerning another structure of a capacity-of-battery reporting means.

Furthermore, instead of the liquid crystal panel 3, a light-emitting diode 39 may be, as shown in FIG. 7, used as a capacity-of-battery reporting means to report an amount of electrical energy contained in a battery. The light-emitting diode 39 may be such that as a voltage given by the battery falls, it gets darker. Otherwise, when the battery voltage falls below a predefined value, it may be lit or flicker. Otherwise, when the battery voltage falls below the predefined value, the color of emitted light may change from blue to red or a second light-emitting diode, which is not shown, different from the light-emitting diode 39 may be lit or put out.

Figure 8:
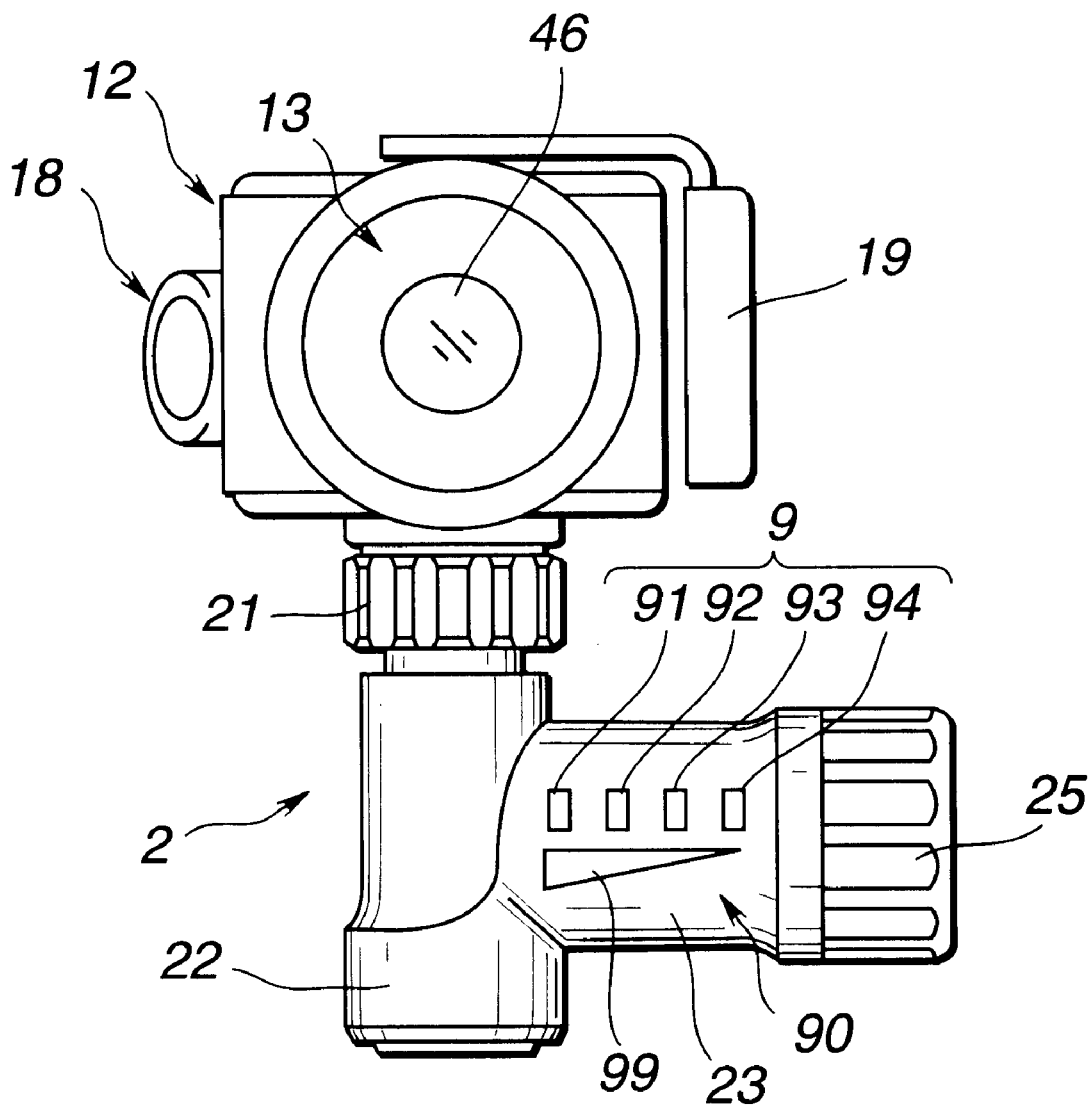
FIG. 8 is an explanatory diagram concerning still another structure of the capacity-of-battery reporting means.

As shown in FIG. 8, a plurality of indication elements 9 may be used to constitute a level meter 90 whose driven and lit state changes along with a rise or fall of a voltage given by a battery. In this case, light-emitting diodes (LEDs) 91, 92, 93, and 94 may be used to indicate the level of a voltage given by the battery 5 while classifying it into either of two categories; a category of effective-use voltages and a category of alarm voltages.

LEDs indicating effective-use voltages are, for example, LEDs that glow in green. The three LEDs 91, 92, and 93 are juxtaposed. When the battery is fully charged, the three LEDs 91, 92, and 93 are lit simultaneously. As the voltage given by the battery 5 falls, the LEDs 91, 92, and 93 are switched off one by one in that order. The capacity of the battery 5 is thus indicated.

When the voltage given by the battery 5 drops, if the last LED 93 indicating an effective use voltage is off, an LED 94 indicating an alarm voltage starts flickering. The indication of an alarm voltage implies that the battery is almost exhausted. For example, when an amount of electrical energy remaining in a battery reaches an amount of electrical energy required to examine one case using the endoscope, the alarm indication is carried out.

The LED 94 indicating an alarm may be separated from the group of the LEDs 91, 92, and 93 indicating the effective use voltages or may glow in an alarm color such as red. The LED 94 is thus distinguished from the other LEDs.

Moreover, a scale 99 shaped like a right-angled triangle whose base is located by the side of the lamp stowage portion 22 may be placed adjacent the LEDs 91, 92, 93, and 94 so that the meaning of indication can be grasped intuitively. This would help discern the capacity of the battery on sight of an LED that is lit or flickering.

The liquid crystal panel 3 or indication elements 9 in the present embodiment may be disposed in an opening window, which is not shown, bored in the battery stowage portion 23 in a watertight manner. Otherwise, the whole housing member of the battery-powered light source 2 including the battery stowage portion 23 may be molded using a transparent resin. The liquid crystal panel 3 or indication elements 9 may be incorporated in the housing member so that the contents of indication can be observed through the transparent housing member. Even this structure can be realized in a watertight manner.

The endoscope to which the battery-powered light source 2 of the present embodiment is attached is an optical endoscope. In the optical endoscope, the objective lens 43 included in the distal portion 14 picks up an object image, and the optical object image is propagated to the end of the eyepiece unit 13 over the image guide fiber bundle 41. Thus, an object is observed visually through the observation window 46 by way of the eyepiece 44. Alternatively, the battery-powered light source 2 of the present invention may be freely detachably attached to an electronic endoscope. In the electronic endoscope, an imaging device such as a CCD is incorporated in the distal part of an insertion portion, an object image is projected on the imaging device and photoelectrically converted, and a resultant image signal is processed in order to produce an endoscopic image.

The second embodiment of the present invention will be described with reference to FIG. 9 and FIG. 10.

In the first embodiment, the liquid crystal panel 3 or indication elements 9 serving as a capacity-of-battery reporting means for reporting the amount of electrical energy contained in the battery 5 are positioned on the side of the eyepiece unit 13 so that they will be opposed to an observer's face during observation. By contrast, in the present embodiment, the capacity-of-battery reporting means is located in the eyepiece unit 13 of the endoscope 1. The same reference numerals will be assigned to members identical to those of the first embodiment. The description of the members will be omitted.

Figure 9:
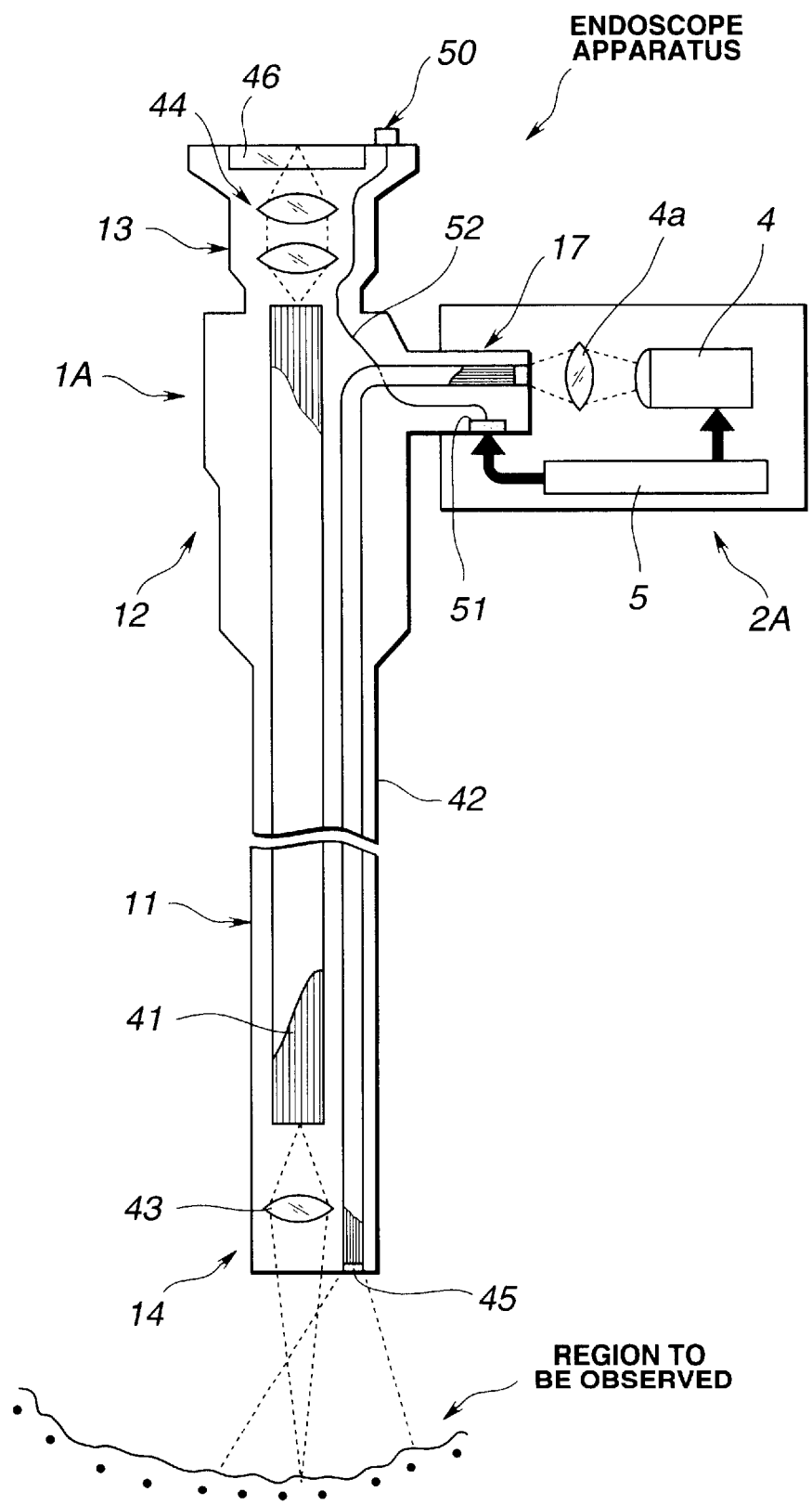
FIG. 9 and FIG. 10 show the second embodiment of the present invention.

In an endoscope 1A of the present embodiment shown in FIG. 9, when a battery-powered light source 2A is coupled to the light guide base 17 jutting out of the control section 12, a driving signal output from the drive circuit 8 is transmitted via en electrical contact 51 over a signal line 52. The signal line 52 is passed through the control section 12 to an indication unit 50 composed of the indication elements 9 such as LEDs formed in a watertight manner adjacently to the observation window 46 formed in the eyepiece unit 13.

Figure 10:
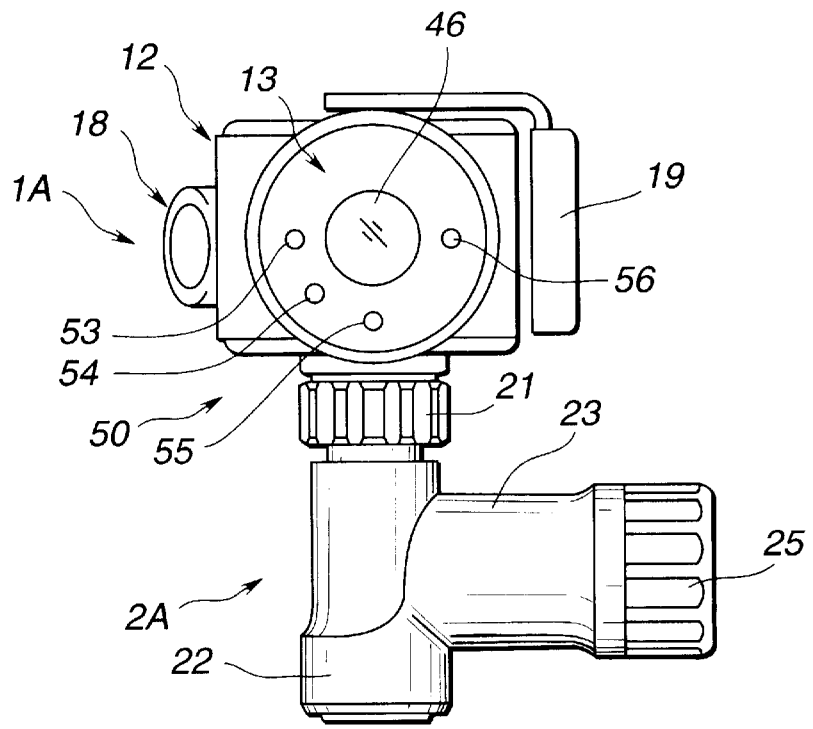

As shown in FIG. 10, for example, three LEDs 53, 54, and 55 and one LED 56 are arranged as the indication elements 9 constituting the indication unit 50 on the perimeter of the observation window 46 of the eyepiece unit 13. The LEDs 53, 54, and 55 and LED 56 indicate, similarly to those described in conjunction with FIG. 8, effective use voltages and an alarm voltage.

The three LEDs 53, 54, and 55 indicating the effective use voltages are arranged at intervals of about 45°. The levels of a voltage given by the battery 5 are associated in advance with the positions of the LEDs 53, 54, and 55 to be lit. Even when any one of the LEDs 53, 54, and 55 is lit, an amount of remaining electrical energy can be discerned. Moreover, an LED 56 intended to indicate an alarm voltage may be, like the one described in conjunction with FIG. 8, separated from the other LEDs or may be designed to glow in an alarm color such as red. The LED 56 is thus distinguished from the other LEDs 53, 54, and 55.

For indicating the effective use voltages, as described in relation to the first embodiment, the LEDs 53, 54, and 55 may be lit simultaneously and then put out one by one.

Operations to be exerted by the endoscope apparatus will be described below.

The battery-powered light source 2A having the foregoing components is coupled and fixed to the endoscope 1A, thus constituting the endoscope apparatus. The battery-powered light source 2A is swiveled on the control section 12 in order to light the lamp 4. A driving signal output from the drive circuit 8 is transmitted to the indication elements 9 constituting the indication unit 50 on the eyepiece unit 13 over the signal line 52. Consequently, the capacity of the battery 5 is indicated.

A user intending to observe a region looks through the observation window 46 of the eyepiece unit 13. The user then checks the lit state of any of the LEDs 53, 54, 55, and 56 which are arranged on the perimeter of the observation widow 46 so as to see the amount of electrical energy remaining in the battery. Moreover, even when the user is engaged in observation, the user need not withdraw his/her face from the eyepiece unit 13 but can readily check the amount of electrical energy remaining in the battery.

As mentioned above, the present embodiment can not only provide the same advantage as the first embodiment but also makes it possible to readily check an amount of electrical energy remaining in a battery without the necessity of withdrawing a face from the eyepiece unit. Consequently, unexpected exhaustion of a battery can be prevented effectively.

Moreover, since the capacity-of-battery reporting means for notifying of an amount of electrical energy remaining in a battery is located on the eyepiece unit, the battery-powered light source can be designed compactly.

Figure 11:
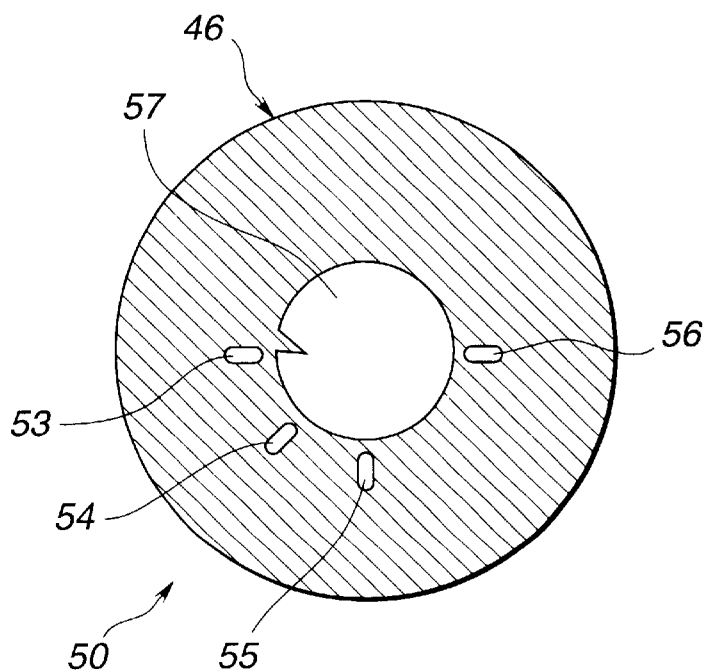
FIG. 11 is an explanatory diagram concerning an indication unit formed inside the eyepiece unit.

As shown in FIG. 11, instead of arranging the LEDs 53, 54, 55, and 56 on the perimeter of the observation window 46 in a watertight manner, the LEDs 53, 54, 55, and 56 may be placed inside the eyepiece unit 13. In this structure, when the observation window 46 of the eyepiece unit 13 is looked through, the indication elements such as LEDs are seen around an endoscopic image 57.

When the LEDs are placed inside the eyepiece unit, there is provided, in addition to the same advantage as the second embodiment, such an advantage that the watertightness of the eyepiece unit improves. This is because it becomes unnecessary to arrange the indication elements such as LEDs on the outer surface of the eyepiece unit in a watertight manner.

Moreover, a user can check an amount of electrical energy remaining in a battery without withdrawing his/her face from the eyepiece unit, that is, while viewing an endoscopic image. The user can observe a region of interest while being conscious of an amount of electrical energy remaining in a battery all the time. Consequently, it can be prevented more reliably that a user forgets to check an amount of electrical energy remaining in a battery.

Instead of forming the indication unit on the control section of the endoscope, a pager motor generally employed in portable telephones or the like may be incorporated as a capacity-of-battery reporting means in the control section of the endoscope. Driving power may then be supplied to the motor synchronously with an alarm driving signal sent from the battery stowage portion. According to this structure, an alarm warning against an amount of electrical energy remaining in a battery is not given visually but vibrations generated by driving the motor are propagated to the hand by which the endoscope is grabbed. Thus, the alarm warning against exhaustion of a battery can be more reliably given to a user.

Moreover, a loudspeaker and a driving means for driving the loudspeaker may be incorporated as a capacity-of-battery reporting means in the control section of the endoscope or the battery-powered light source. Driving power is then supplied to the driving means synchronously with a drive signal output from the battery stowage portion. Consequently, an alarm warning against an amount of electrical energy remaining in a battery can be more reliably given to a user by voice.

The third embodiment of the present invention will be described with reference to FIG. 12.

In the present embodiment, a liquid crystal monitor 61 for displaying an endoscopic image is included in a battery-powered light source 2B. The capacity of the battery 5 incorporated in the battery-powered light source 2B is indicated at the same time when an endoscope image is displayed. The same reference numerals will be assigned to members identical to those of the second embodiment. The description of the members will be omitted.

An endoscope 1B has an eyepiece unit 13 composed of, as mentioned in conjunction with FIG. 9, an eyepiece 44, a half mirror that is not shown, and a solid-state imaging device. The eyepiece 44 converges a view image transmitted over the image guide fiber bundle 41 on an operator's pupil. The half mirror projects the view image converged by the eyepiece 44. The solid-state imaging device photoelectrically converts the view image projected by the half mirror. A signal line is extending from the solid-state imaging device, passed through the control section 12, and routed to the liquid crystal monitor 61 via an electrical contact that is coupled to the battery-powered light source 2B and formed on the light guide base.

Figure 12:
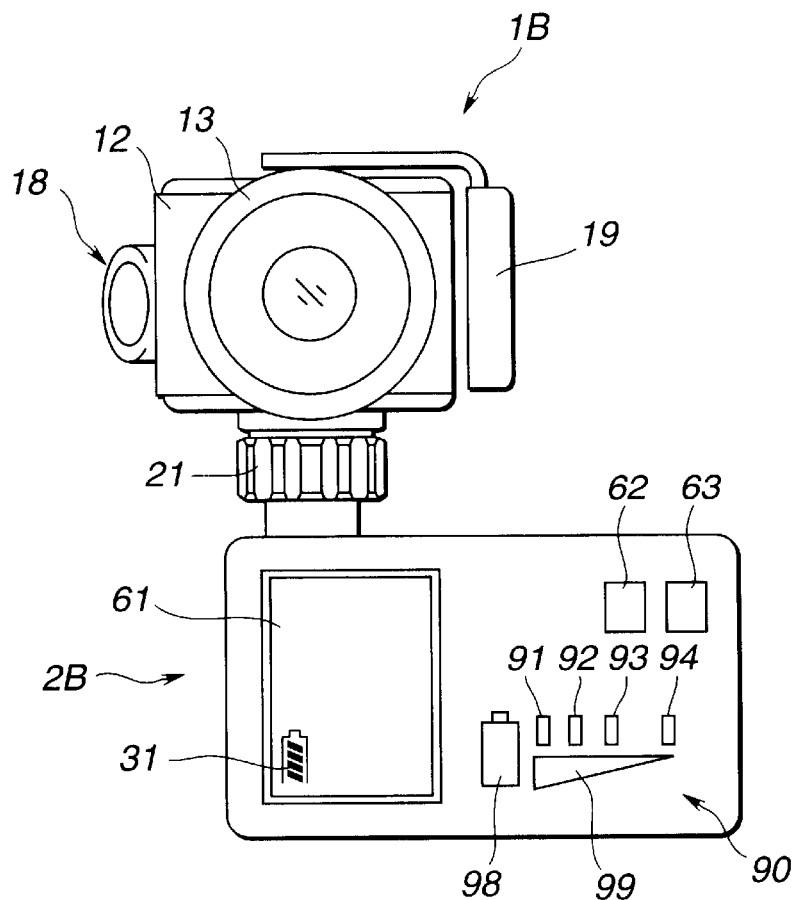
FIG. 12 is an explanatory diagram concerning the components of a battery-powered light source having a capacity-of-battery reporting means, which reports the capacity of a battery, and a liquid crystal monitor, thus explaining the third embodiment of the present invention.

As shown in FIG. 12, when the battery-powered light source 2B is attached to the endoscope 1B, an optical image projected on the solid-state imaging device is photoelectrically converted into an electric signal. The electric signal is output to a video processing circuit, which is not shown, united with the liquid crystal monitor 61 via a contact pin formed on the light guide base. Consequently, the endoscopic image is displayed on the liquid crystal monitor 61. Driving power for driving the solid-state imaging device and liquid crystal monitor 61 is supplied from the battery 5 built in the battery-powered light source 2B.

The battery-powered light source 2B of the present embodiment has a lamp switch 62, a monitor switch 63, and a level meter 90. The lamp switch 62 is used to light the built-in lamp 4. The monitor switch 63 is used to activate the liquid crystal monitor 61. The level meter 90 is, like the one described in conjunction with FIG. 8, composed of LEDs 91, 92, 93, and 94, and a scale 99. The liquid crystal monitor 61 is activated only when the lamp 4 is lit. Reference numeral 98 denotes a battery mark.

When the lamp switch 62 is turned on, the lamp 4 is lit. As mentioned in conjunction with FIG. 8, any of the LEDs 91, 92, 93, and 94 constituting the level meter 90 is driven to light. Thereafter, when the monitor switch 63 is turned on, the LED of the level meter 90 that has been driven to light is put out and the liquid crystal monitor 61 is activated. An endoscopic image is then displayed in enlargement on the display screen of the liquid crystal monitor 61. Besides, an indicator 31 indicating an amount of electrical energy remaining in a battery is displayed in the corner of the display screen.

Incidentally, the level meter 90 and liquid crystal monitor 61 are positioned so that a user will confront them during observation using the endoscope.

As mentioned above, the liquid crystal monitor for displaying a view image in enlargement is included in the battery-powered light source. Even when a user has withdrawn his/her face from the eyepiece unit, the user can view an endoscopic image or check the capacity of a battery. This leads to improved maneuverability of the endoscope apparatus. Moreover, an examination can be conducted with an endoscopic image, which is displayed in enlargement on the liquid crystal monitor, viewed in common among many people.

Moreover, if an amount of electrical energy remaining in a battery almost runs out during use of the liquid crystal monitor, the monitor switch is turned off. Visual observation is then continued with the lamp alone lit. Thus, observation can be carried out continuously. The other operations and advantages are identical to those of the previous embodiments.

Figure 13:
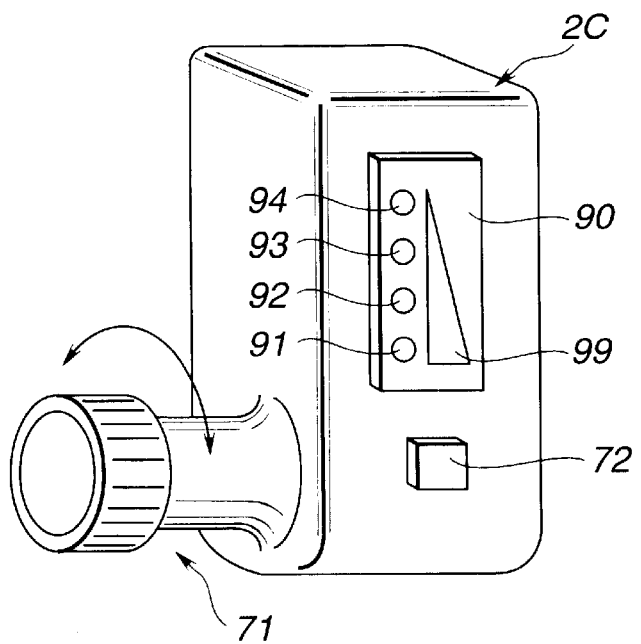
FIG. 13 is an explanatory diagram concerning the battery-powered light source.

The fourth embodiment of the present invention will be described with reference to FIG. 13 and FIG. 14.

A battery-powered light source 2C of the present embodiment is shaped, for example, like a box. A connector portion 71 to be coupled to an endoscope is jutting out from one side of the battery-powered light source 2C. The level meter 90 and a remaining energy indication switch 72 are formed on the face of the battery-powered light source. The level meter 90 for indicating the capacity of a battery is, like the one shown in FIG. 8, composed of the LEDs 91, 92, 93, and 94 and the scale 99. The remaining energy indication switch 72 is used to indicate the capacity of a battery using the level meter 90, that is, to indicate an amount of electrical energy remaining in the battery.

The level meter 90 has the LEDs 91, 92, 93, and 94 lined in tandem. The scale 99 lies by the side of the LEDs in order to help intuitively grasp the meaning of indication provided by the level meter 90.

The scale 99 is shaped like, for example, a right-angled triangle whose base is opposed to the connector portion 71. When the LED 91 lying by the side of the base is lit, it means that the battery is fully charged. When the LED closer to the apex of the scale 99 is lit, it means that the amount of electrical energy remaining in the battery is limited. When the LED 94 closest to the apex of the scale 99 is lit, the amount of electrical energy remaining in the battery is small or too small to use the battery-powered light source 2C.

Alternatively, the four LEDs 91, 92, 93, and 94 may be lit simultaneously and then put out one by one. Thus, the amount of electrical energy remaining in the battery may be indicated.

Figure 14:
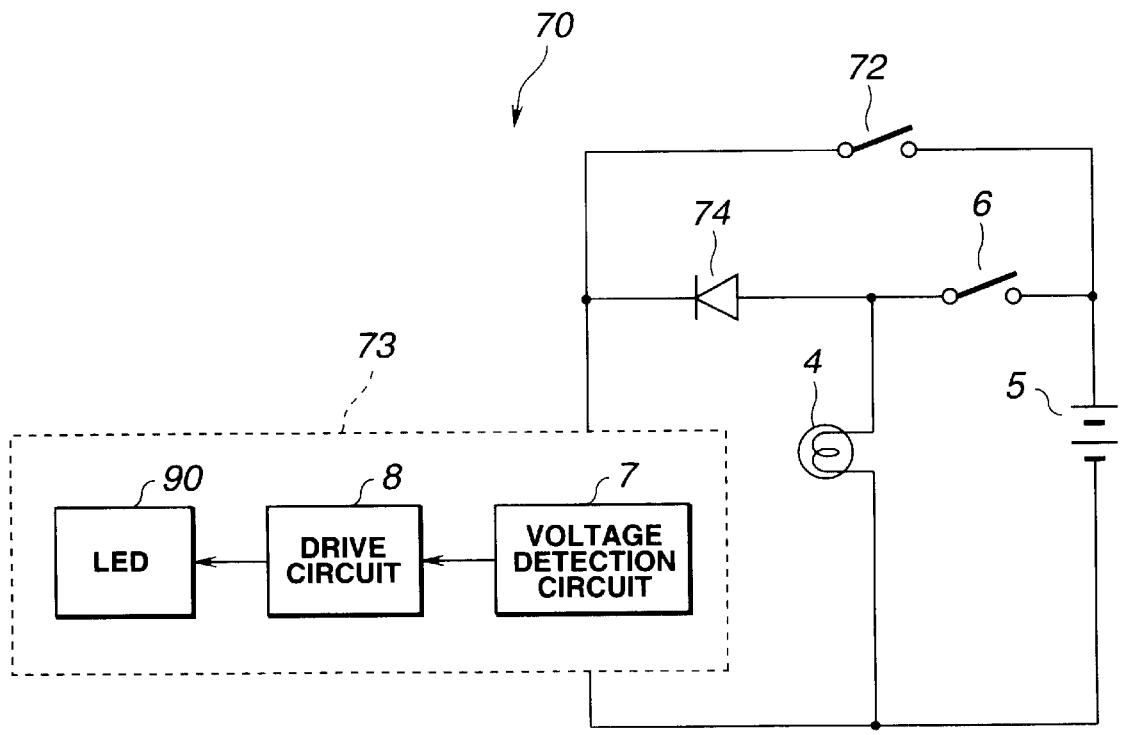
FIG. 14 is a block diagram for explaining a light source operation circuit included in the battery-powered light source.

By the way, as shown in FIG. 14, a light source operation circuit 70 incorporated in the battery-powered light source 2C of the present embodiment has the illumination lamp 4 and a remaining battery energy indication circuit 73 connected in parallel with the battery 5. The remaining battery energy indication circuit 73 lights the LEDs 91, 92, 93, and 94 to indicate an amount of electrical energy remaining in a battery. The power switch 6 is connected on a line that conducts electricity to the illumination lamp 4. The remaining energy indication switch 72 is connected on a line that conducts electricity to the remaining battery energy indication circuit 20.

Moreover, according to the present embodiment, the remaining battery energy indication circuit 73 and remaining energy indication switch 72 are connected via a diode 74 between the illumination lamp 4 and switch 6. Even when the remaining energy indication switch 72 is turned off, if the switch 6 is turned on, the remaining battery energy indication circuit 73 conducts. Any LED of the level meter 90 is driven to light.

Furthermore, since the diode 74 is included, when the switch 6 is turned off, even if the remaining energy indication switch 72 is turned on, the illumination lamp 4 does not conduct.

The remaining battery energy indication circuit 73 includes the voltage detection circuit 7 and drive circuit 8. The voltage detection circuit 7 serves as an electrical battery energy detecting means for detecting a voltage given by the battery 5. The drive circuit 8 drives and lights the level meter 90, which is composed of the LEDs 91, 92, 93, and 94, according to a voltage detected by the voltage detection circuit 7.

Owing to the light source operation circuit 70 having the foregoing components, when the remaining energy indication switch 72 is turned on, the battery-powered light source 2C drives and lights the level meter 90 irrespective of the on or off state of the switch 6. The battery-powered light source 2C thus has the capability of a capacity-of-battery reporting means. The other components are identical to those of the aforesaid embodiments. The same reference numerals will be assigned to the identical components. The description of the components will be omitted.

The endoscope 2 and battery-powered light source 2C may be separated from each other. Otherwise, the battery-powered light source 2C may be coupled and fixed to the endoscope 1 but the battery-powered light source 2C may have not been swiveled substantially 90° with the connector portion 71 as an axis or rotation. A description will be made of how to indicate the amount of electrical energy remaining in the battery built in the battery-powered light source 2C in this state.

First, the remaining energy indication switch 72 on the battery-powered light source 2C is turned on. This causes the remaining battery energy indication circuit 73 to conduct. The voltage detection circuit 7 detects a voltage given by the battery 5. The drive circuit 8 drives and lights the level meter 90 according to the voltage detected by the voltage detection circuit 7. Thus, the capacity of the battery 5 can be discerned.

When the battery-powered light source 2C coupled and fixed to the endoscope 1 is swiveled substantially 90°, the lamp is lit. In this state, the switch 6 on the battery-powered light source 2C is on, and the remaining battery energy indication circuit 73 is conducting. Although the remaining energy indication switch 72 is not manipulated, the voltage detection circuit 7 detects a voltage given by the battery 5 all the time. The drive circuit 8 drives and lights the level meter 90 according to the voltage detected by the voltage detection circuit 7. The capacity of the battery 5 can be discerned.

As mentioned above, in the battery-powered light source of the present embodiment, even when the power switch is off, if the remaining energy indication switch is manipulated to be turned on, an amount of electrical energy remaining in a battery is indicated with the level meter. A user can therefore readily discern the capacity of the battery irrespective of whether the battery-powered light source is used or unused or whether the battery-powered light source is coupled to or uncoupled from the endoscope.

Before the battery-powered light source is coupled and fixed to the endoscope for use, whether the capacity of a battery is sufficient can be judged. The other operations and advantages are identical to those of the aforesaid embodiments.

Figure 15:
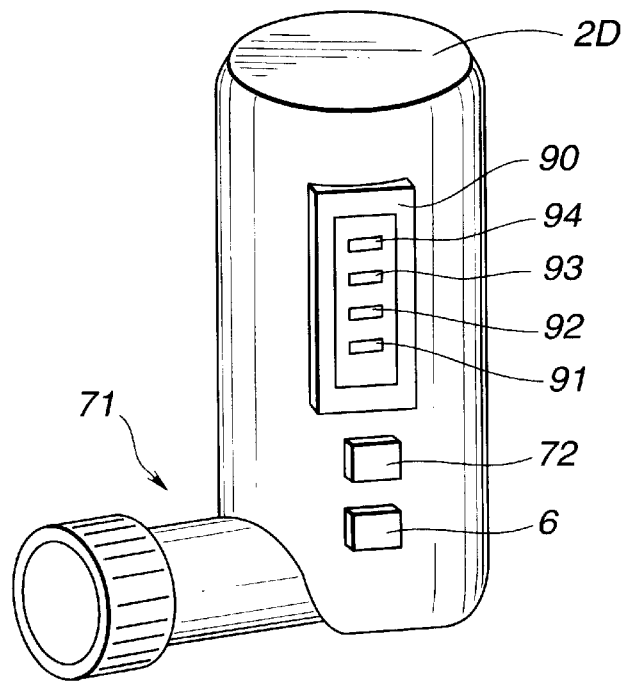
FIG. 15 is an explanatory diagram concerning a battery-powered light source in accordance with the fifth embodiment of the present invention.

The fifth embodiment of the present invention will be described with reference to FIG. 15.

According to the present embodiment, the appearance of a battery-powered light source and a power switch are different from those of the fourth embodiment. The other components are identical to those of the aforesaid embodiments. The same reference numerals will be assigned to the identical components, and the description of the components will be omitted.

As illustrated, a battery-powered light source 2D of the present embodiment is shaped, for example, like a cylinder. The remaining energy indication switch 72 and switch 6 are formed on the surface of the battery-powered light source. The remaining energy indication switch 72 is used to indicate an amount of electrical energy remaining in a battery. A user manipulates the switch 6 for lighting or putting out the illumination lamp 4. The present embodiment includes the light source operation circuit 70 similarly to the fourth embodiment.

When the switch 6 of the battery-powered light source 2D is off, if the remaining energy indication switch 72 is turned on, the remaining battery energy indication circuit 73 conducts. This causes the voltage detection circuit 7 to detect a voltage given by the battery 5. The drive circuit 8 drives and lights the level meter 90 according to the voltage detected by the voltage detection circuit 7. An amount of electrical energy remaining in a battery built in the battery-powered light source 2D is thus indicated.

Moreover, when the battery-powered light source 2D is coupled to the endoscope 1, if the switch 6 of the battery-powered light source 2D is turned on, the illumination lamp 4 is lit and the remaining battery energy indication circuit 73 conducts. Although the remaining energy indication switch 72 is not turned on, the voltage detection circuit 7 always detects the voltage given by the battery 5. The drive circuit 8 drives and lights the level meter 90 according to the voltage detected by the voltage detection circuit 7. An amount of electrical energy remaining in a battery built in the battery-powered light source 2D is thus indicated.

As mentioned above, according to the present embodiment, similarly to the aforesaid embodiments, even when the switch of the battery-powered light source is off, if the remaining energy indication switch is turned on, the level meter is driven to indicate an amount of electrical energy remaining in a battery. A user can readily discern the amount of electrical energy remaining in the battery, and uses the endoscope apparatus with a sufficient amount of electrical energy left in the battery built in the battery-powered light source.

Figure 16:
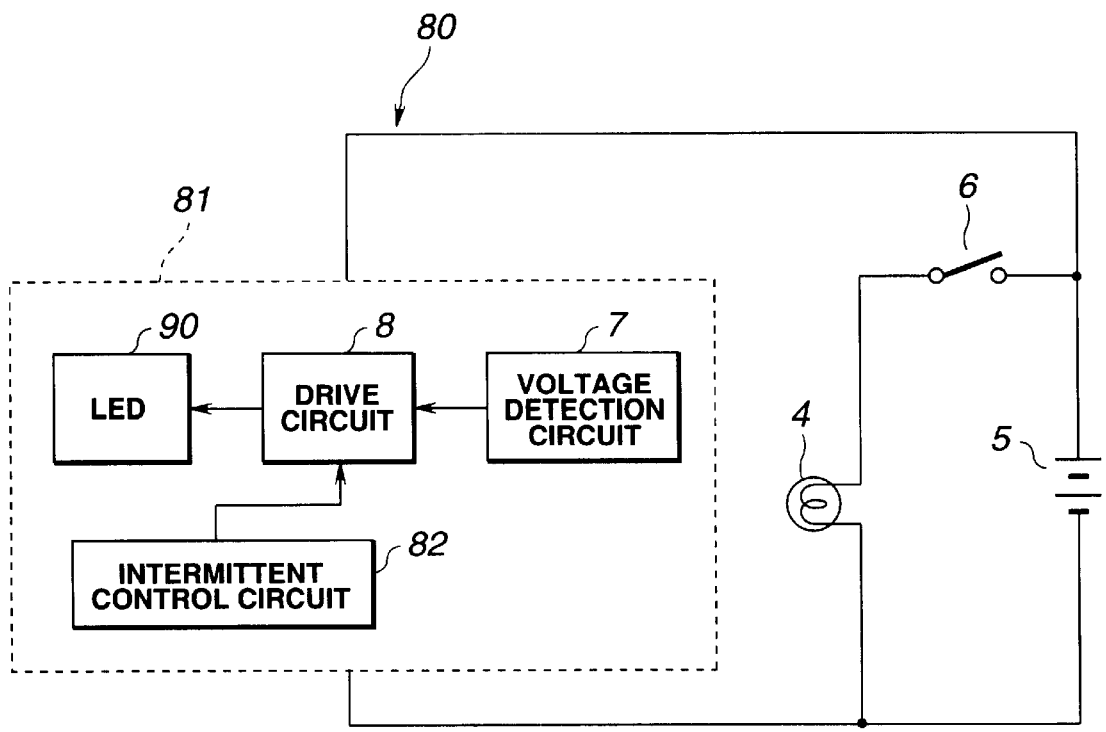
FIG. 16 is a block diagram for explaining a light source operation circuit in accordance with the sixth embodiment of the present invention.

The sixth embodiment of the p resent invention will be described with reference to FIG. 16.

Compared with the fifth embodiment, the present embodiment does not include the remaining energy indication switch 72 and has the light source operation circuit incorporated in the battery-powered light source modified.

As illustrated, a light source operation circuit 80 incorporated in a battery-powered light source of the present embodiment has the illumination lamp 4 and a remaining battery energy indication circuit 81 connected in parallel with the battery 5. The remaining battery energy indication circuit 81 drives and lights the level meter 90 composed of the LEDs 91, 92, 93, and 94 and thus indicates an amount of electrical energy remaining in a battery. The switch 6 is connected on a line that conducts electricity to the illumination lamp 4.

Moreover, the remaining battery energy indication circuit 81 includes the voltage detection circuit 7, the drive circuit 8, and an intermittent lighting control circuit 82. The voltage detection circuit 7 detects a voltage given by the battery 5. The drive circuit 8 drives and lights the level meter 90 according to the voltage detected by the voltage detection circuit 7. The intermittent lighting control circuit 82 gives control to intermittently light the LEDs 91, 92, 93, and 94 constituting the level meter 90 using a timer. Specifically, the LEDs are, for example, lit for ten sec and put out for 50 sec.

According to the present embodiment, the level meter 90 always indicates an amount of electrical energy remaining in a battery irrespective of the on or off state of the switch 6 of the illumination lamp 4. The present embodiment can provide the same advantage s as the aforesaid embodiments.

Moreover, the level meter 90 intermittently indicates an amount of electrical energy remaining in a battery under the control of the intermittent lighting control circuit 82 included in the remaining battery energy indication circuit 81. Current required to permit indication is lower than that required to permit continuous indication.

Figure 17:
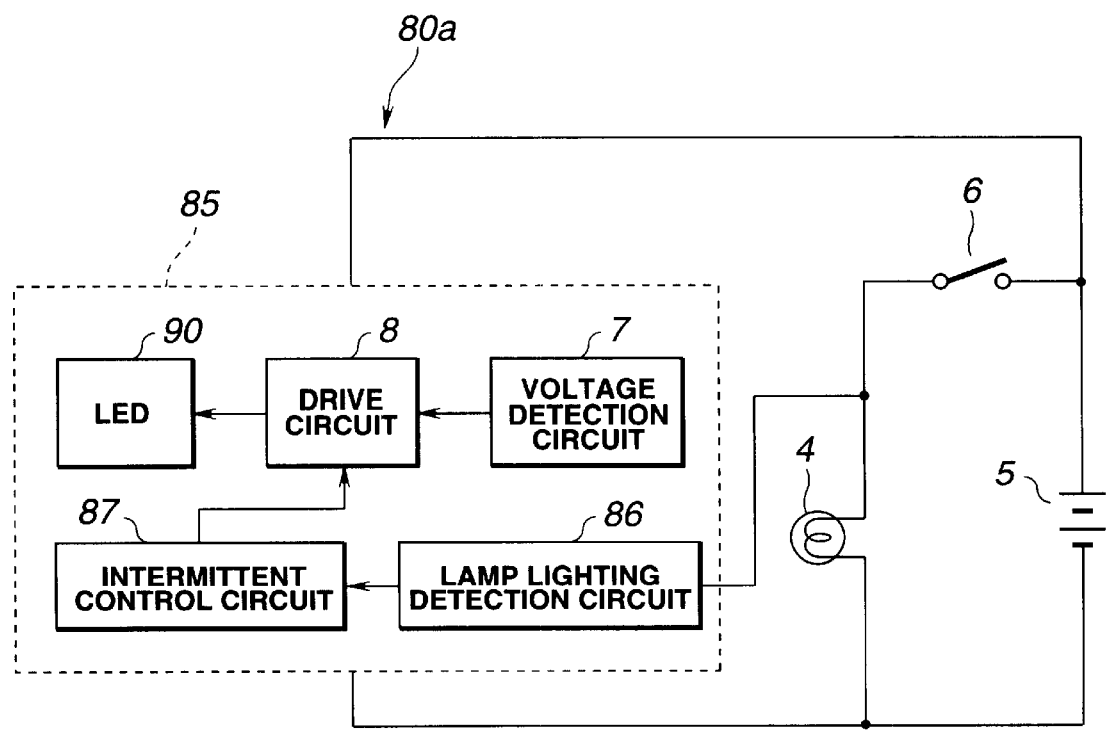
FIG. 17 is a block diagram for explaining a light source operation circuit in accordance with the seventh embodiment of the present invention.

The seventh embodiment of the present invention will be described with reference to FIG. 17.

The present embodiment has a remaining battery energy indication circuit 85 included in a light source operation circuit 80a which is a modification of the remaining battery energy indication circuit included in the sixth embodiment.

As illustrated, the light source operation circuit 8a incorporated in the battery-powered light source of the present embodiment has the illumination lamp 4 and remaining battery energy indication circuit 85 connected in parallel with the battery 5. The remaining battery energy indication circuit 85 drives and lights the level meter 90 composed of the LEDs 91, 92, 93, and 94 and thus indicates an amount of electrical energy remaining in a battery. The switch 6 is connected on a line that conducts electricity to the illumination lamp 4.

Moreover, the remaining battery energy indication circuit 85 includes the voltage detection circuit 7, the drive circuit 8, a lamp lighting detection circuit 6, and an intermittent lighting control circuit 87. The voltage detection circuit 7 detects a voltage given by the battery 5. The drive circuit 8 drives and lights the level meter 90 according to the voltage detected by the voltage detection circuit 7. The lamp lighting detection circuit 86 detects whether the illumination lamp 4 is lit or put out. The intermittent lighting control circuit 87 gives control to intermittently light the LEDs 91, 92, 93, and 94 constituting the level meter according to a signal sent from the lamp lighting detection circuit 86.

When a signal input from the lamp lighting detection circuit 86 indicates that the illumination lamp 4 is lit, the intermittent lighting control circuit 87 gives control to continuously light the LEDs 91, 92, 93, and 94. By contrast, when the signal input from the lamp lighting detection circuit 86 indicates that the illumination lamp 4 is off, the intermittent lighting control circuit 87 gives control to intermittently light the LEDs 91, 92, 93, and 94. Specifically, the LEDs are, for example, lit for ten sec and off for fifty sec.

According to the present embodiment, the level meter 90 indicates an amount of electrical energy remaining in a battery irrespective of whether the switch 6 of the illumination lamp 4 is on or off. The present embodiment can provide the same advantages as the aforesaid embodiments.

Moreover, when the illumination lamp 4 is lit, the level meter indicating an amount of electrical energy remaining in a battery is lit continuously. Therefore, the capacity of the battery 5 can be determined any time with the endoscope put to use. If the battery 5 is exhausted during use of the endoscope, the battery 5 can be speedily replaced with a new one or charged. Otherwise, the battery-powered light source employed may be replaced with another one.

According to the present embodiment, when the illumination lamp 4 is on, an amount of electrical energy remaining in a battery is continuously indicated under the control of the intermittent lighting control circuit 87. When the illumination lamp 4 is off, the amount of electrical energy remaining in the battery is indicated intermittently. Alternatively, the interval during which the amount of electrical energy remaining in the battery is indicated may be modified. Specifically, when the illumination lamp 4 is lit, the level meter may be lit during a shorter interval. When the illumination lamp 4 is put out, the level meter may be put out during a longer interval. In this case, consumption of energy in the battery can be reduced compared with that required to continuously indicate the amount of electrical energy remaining in the battery.

The eighth embodiment of the present invention will be described with reference to FIG. 18 to FIG. 20.

When a chargeable battery is used as the battery 5, the battery is characterized in that when the battery is fully discharged, the performance thereof deteriorates, or in other words, the apparent capacity thereof decreases. According to the present embodiment, a light source operation circuit incorporated in a battery-powered light source indicates a charge time properly so that the next charging can be carried out before the chargeable battery is fully discharged. The same reference numerals will be assigned to members identical to those of the aforesaid embodiments. The description of the members will be omitted.

Figure 18:
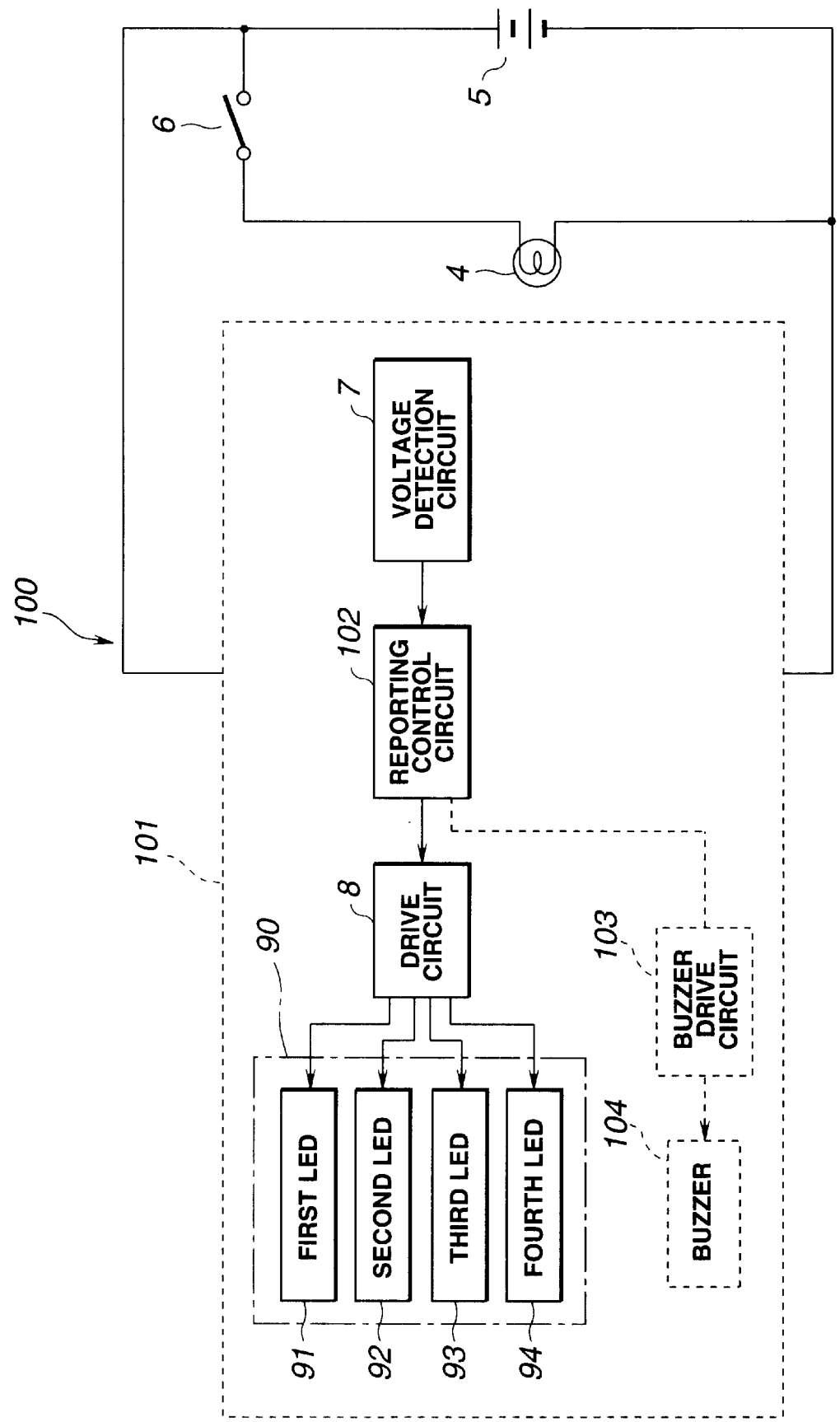
FIG. 18 to FIG. 20 show the eighth embodiment of the present invention.

As shown in FIG. 18, a light source operation circuit 100 incorporated in a battery-powered light source of the present embodiment has the illumination lamp 4 and a remaining battery energy indication circuit 101 connected in parallel with the battery 5. The remaining battery energy indication circuit 101 drives and lights the level meter 90 composed of the LEDs 91, 92, 93, and 94 and thus indicates an amount of electrical energy remaining in a battery. The switch 6 is connected on a line that conducts electricity to the illumination lamp 4.

The remaining battery energy indication circuit 101 includes the voltage detection circuit 7, a reporting control circuit 102, and the drive circuit 8. The voltage detection circuit 7 detects a voltage given by the battery 5. The reporting control circuit 102 follows a remaining battery energy indication program that will be described later, selects any of the LEDs 91, 92, 93, and 94 to be lit according to the voltage detected by the voltage detection circuit 7, and outputs a signal indicating a selected LED. The drive circuit 8 is driven with a signal output from the reporting control circuit 102, and lights or puts out the LEDs 91, 92, 93, and 94 constituting the level meter 90.

When the battery 5 is fully charged, the remaining battery energy indication circuit 101 lights the LED 91 according to the remaining battery energy indication program. When the battery 5 is not fully charged but need not be charged, the LED 92 is lit. If the charge time when the battery 5 should be charged has come, the LED 93 is lit. If the battery 5 may become unusable soon because of a little amount of remaining electrical energy, the LED 94 is lit.

Figure 19:
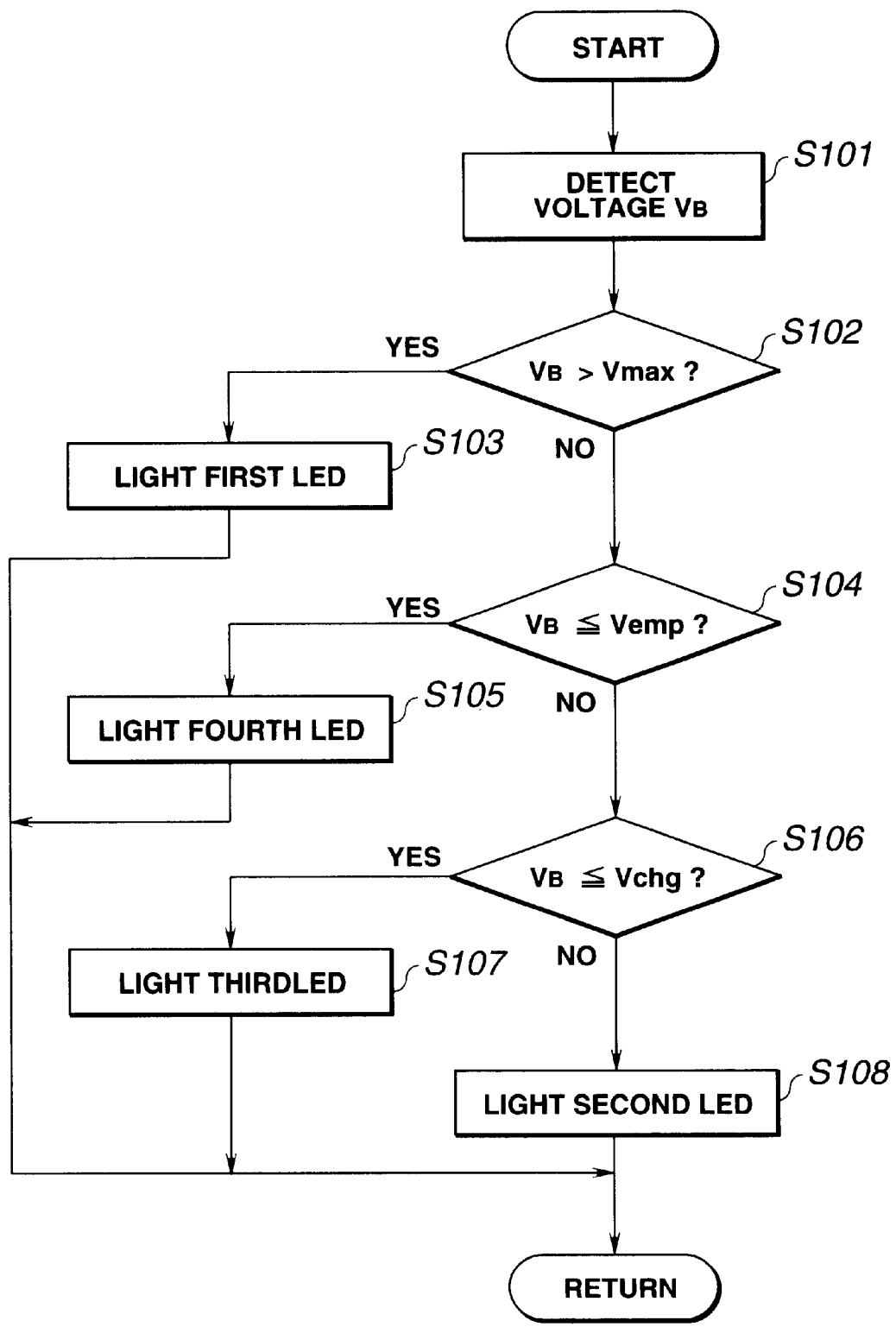
Figure 20:
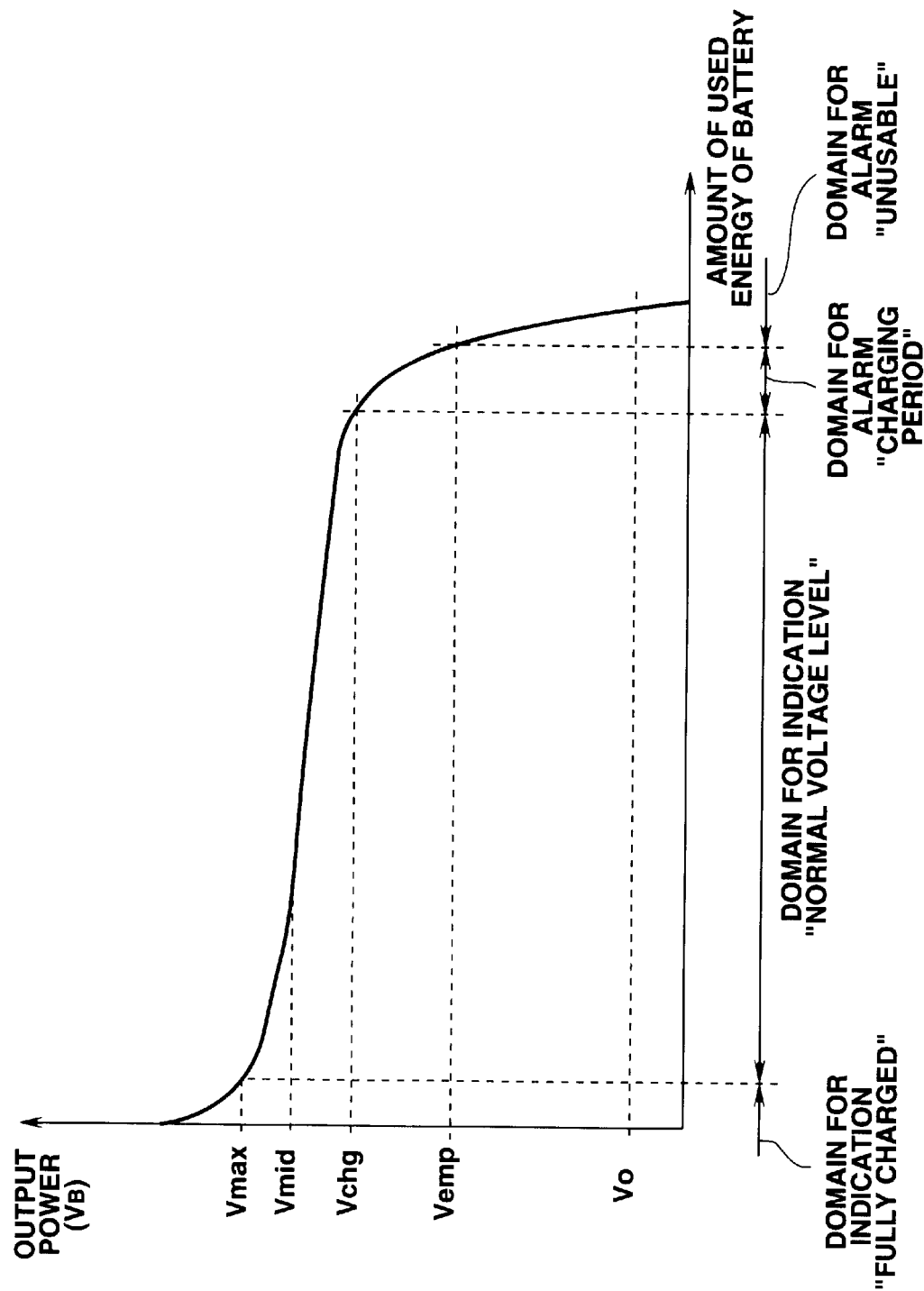

In short, the remaining battery energy indication program to be followed by the remaining battery energy indication circuit 101 is a program to be executed repeatedly as described in the flowchart of FIG. 19.

First, at step S101, the voltage detection circuit 7 detects a voltage $V_B$ currently given by a battery. Control is then passed to step S102.

At step S102, the battery voltage $V_B$ is compared with a voltage value $V_{max}$. When the battery voltage $V_B$ is higher than the voltage value $V_{max}$, control is passed to step S103. The LED 91 for reporting that the battery is fully charged is lit, and the program is exited. Incidentally, the voltage value $V_{max}$ is a pre-set voltage value that is detected when the battery 5 has substantially not been used yet.

By contrast, if it is found at step S102 that the battery voltage $V_B$ is equal to or smaller than the voltage value $V_{max}$, control is passed to step S104. At step S104, the battery voltage $V_B$ is compared with a voltage value $V_{emp}$. If the battery voltage $V_B$ is equal to or smaller than the voltage value $V_{emp}$, control is passed to step S105. The LED 94 for alarming that the battery is unusable is lit and the program is exited. Incidentally, the voltage value $V_{emp}$ is, as shown in FIG. 20, a pre-set voltage value indicating that if the battery 5 use continues, the battery would become unusable soon. Moreover, the voltage value $V_{emp}$ indicates that the possibility that if the battery use continues, the performance thereof may deteriorate (apparent capacity thereof would decrease).

By contrast, if it is found at step S104 that the battery voltage $V_B$ is higher than the voltage value $V_{emp}$, control is passed to step S106. At step S106, the battery voltage $V_B$ is compared with a voltage value $V_{chg}$. If the battery voltage $V_B$ is equal to or smaller than the voltage value $V_{chg}$, control is passed to step S107. The LED 93 for reporting that the charge time when the battery 5 should be charged has come is lit and the program is exited. Incidentally, the voltage value $V_{chg}$ is, as shown in FIG. 20, a maximum value of a voltage calculated in advance in consideration of the characteristic of a battery that should be charged right away. Moreover, when the LED 92 is lit, the battery voltage equals to $V_{mid}$ that is an intermediate value between $V_{max}$ and $V_{chg}$.

If it is found at step S106 that the battery voltage $V_B$ is higher than the voltage $V_{chg}$, control is passed to step S108. The LED 92 for indicating that the battery 5 is not fully charged but need not be charged is lit and the program is exited.

As mentioned above, according to the present embodiment, in addition to the advantages of the aforesaid embodiments, the states of a battery can be reported with greater precision. This enables a user to charge the battery on an optimal occasion.

In the present embodiment, four LEDs are used to report the states of a battery. The number of LEDS may be three. Otherwise, five or more LEDs may be used to report the states of the battery 5 more precisely.

Moreover, the present invention is not limited to the mode in which LEDs are lit for reporting the states of a battery. Alternatively, LEDs may be flickered for reporting the states of the battery.

Furthermore, an interval during which an LED is lit may be varied depending on whether an amount of electrical energy remaining in a battery is large or small.

As indicated with a dashed line in FIG. 18, a buzzer drive circuit 103 and a buzzer 104 may be included. The reporting control circuit 102 may cause the buzzer 104 to sound for reporting a state of a battery. Otherwise, a vibrator incorporated in portable telephones or the like may be used to report a state of a battery. When the vibrator or buzzer is used for reporting, an operator becomes aware of an amount of electrical energy remaining in a battery without the necessity of looking at an indicator during endoscopic observation. The operator will therefore be relieved from a nuisance of checking the indication.

The ninth embodiment of the present invention will be described with reference to FIG. 21 and FIG. 22.

Compared with the eighth embodiment, the present embodiment is intended to exert a different operation and provide a different advantage by modifying the remaining battery energy indication circuit included in the light source operation circuit.

Figure 21:
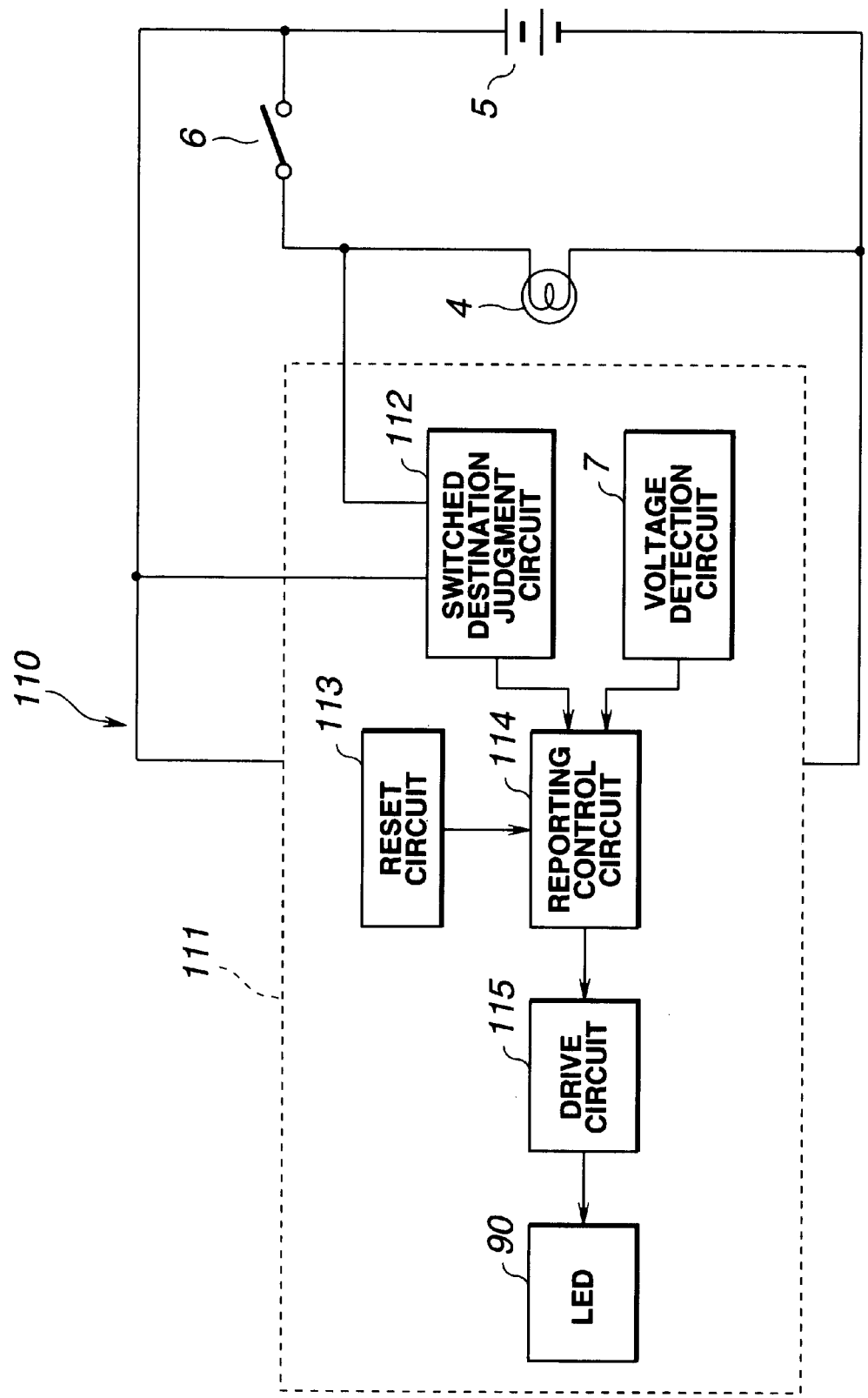
FIG. 21 and FIG. 22 show the ninth embodiment of the present invention.

As shown in FIG. 21, a light source operation circuit 110 incorporated in a battery-powered light source of the present embodiment has the illumination lamp 4 and a remaining battery energy indication circuit 111 connected in parallel with the battery 5. The remaining battery energy indication circuit 111 drives and lights the level meter 90 composed of the LEDs 91, 92, 93, and 94 and thus indicates the amount of electrical energy remaining in the battery. The switch 6 is connected on a line that conducts electricity to the illumination lamp 4.

Moreover, a node between the illumination lamp 4 and switch 6 and a line conducting electricity to the remaining battery energy indication circuit 111 are connected to a switched destination judgment circuit 112 included in the remaining battery energy indication circuit 111.

The remaining battery energy indication circuit 111 includes the voltage detection circuit 7, the switched destination judgment circuit 112, a reset circuit 113, a reporting control circuit 114, and a drive circuit 115. The voltage detection circuit 7 detects a voltage given by the battery 5. The switched destination judgment circuit 112 detects whether the remaining battery energy indication circuit 111 or illumination lamp 4 is conducting. The reset circuit 113 outputs a reset signal when the battery 5 is replaced with another. The reporting control circuit 114 follows a remaining battery energy indication program that will be described later so as to output a control signal according to input signals sent from the voltage detection circuit 7, switched destination judgment circuit 112, and reset circuit 113. The control signal is used to light or put out the LEDs 91, 92, 93, and 94. The drive circuit 115 is driven with a signal sent from the reporting control circuit 114, and lights or puts out the LEDs 91, 92, 93, and 94 constituting the level meter 90.

The remaining battery energy indication circuit 111 follows the remaining battery energy indication program. After the battery 5 is replaced with another, before intermittent indication is started using the LEDs 91, 92, 93, and 94, continuous indication is carried out for a certain time, for example, 60 sec.

Specifically, the remaining battery energy indication program for giving instructions to the remaining battery energy indication circuit 111 is restarted when the battery 5 is replaced with a new one.

Figure 22:
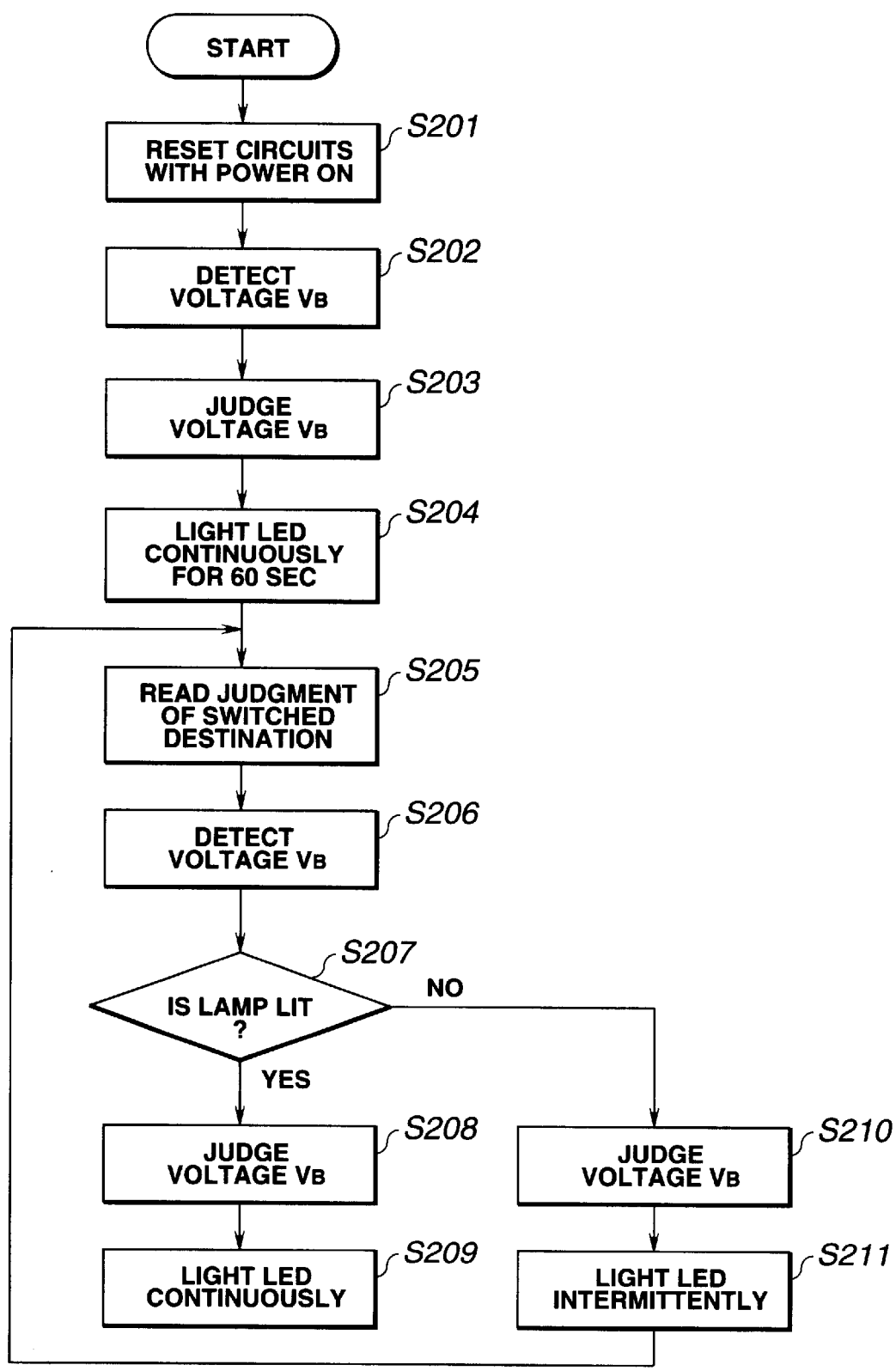

As described in FIG. 22, at step S201, the program is reset in response to a reset signal sent from the reset circuit 113 with the power supply turned on. Control is then passed to step S202.

At the step S202, the voltage detection circuit 7 detects by voltage $V_B$ given a the battery. Control is then passed to step S203. The amount of electrical energy remaining in the battery is indicated with the battery voltage $V_B$. Any of the LEDs 91, 92, 93, and 94 constituting the level meter 90 which is to be lit is determined. The specific procedure of selecting an LED is as per the one described in relation to the eighth embodiment.

Control is then passed to step S204. The LED determined at step S203 is lit continuously for, for example, 60 sec, and control is passed to step S205.

At the step S205, a signal indicating whether the illumination lamp 4 is lit by turning the switch 6 on is read from the switched destination judgment circuit 112. Control is then passed to step S206. The voltage detection circuit 7 detects the battery voltage $V_B$, and control is passed to step S207.

At the step S207, the signal read at step S205 is judged, that is, whether the illumination lamp 4 is lit by turning the switch 6 on is judged. If the illumination lamp 4 is lit, control is passed to step S208. Similarly to the step S203, the amount of electrical energy remaining in the battery is indicated with the battery voltage $V_B$ detected at step S206. Any of the LEDs 91, 92, 93, and 94 constituting the level meter 90 to be lit is determined, and control is passed to step S209. The LED is lit continuously, and the processing started at the step S205 is repeated.

By contrast, if it is judged at step S207 that the illumination lamp 4 is off, control is passed to step S210. Similarly to the step S203, the amount of electrical energy remaining in the battery is indicated with the battery voltage $V_B$ detected at the step S206. Any of the LEDs 91, 92, 93, and 94 constituting the level meter 90 to be lit is determined, and control is passed to step S211. The LED is lit intermittently. Specifically, for example, the LED is lit for ten sec and put out for 50 sec. The processing started at the step S205 is then repeated again.

As mentioned above, the present embodiment can provide the same advantages as those provided by the eighth embodiment. In addition, since an LED is lit continuously after a battery is replaced with another, the amount of electrical energy remaining in the battery 5 can be judged immediately. If the amount of electrical energy remaining in the battery 5 is insufficient, the battery 5 may be able to be recharged or replaced with a new one.

Even in the present embodiment, when the illumination lamp 4 is turned off, if intermittent lighting is carried out continuously, the battery is exhausted. The intermittent lighting may be halted automatically with the passage of a pre-set time. In this case, the pre-set time is set so that the intermittent lighting will continue until cleaning and disinfection of an endoscope is completed after completion of an endoscopic examination.

Moreover, in the aforesaid embodiments, LEDs are lit to report the states of a battery. Alternatively, an LCD may be used to display the states of a battery. Moreover, as described in relation to the eighth embodiment, a sound generated by a buzzer or vibrations generated by a vibrator may be used in combination with lighting of LEDs or may be used solely.

The tenth embodiment of the present invention will be described with reference to FIG. 23 to FIG. 25.

In the aforesaid embodiments, an amount of electrical energy remaining in a battery is indicated as an index. In the present embodiment, a remaining usable time of a battery is also indicated.

Figure 23:
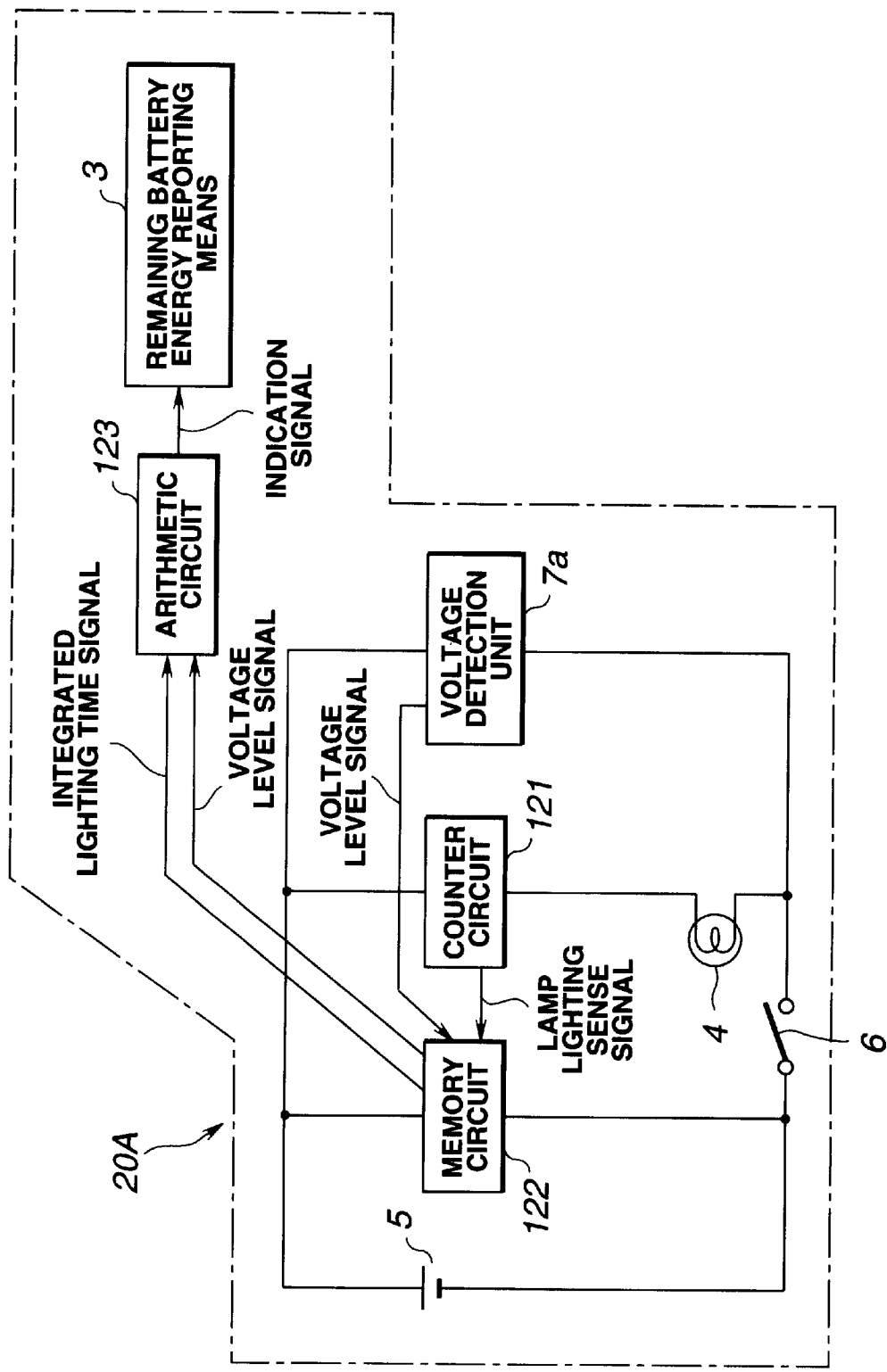
FIG. 23 to FIG. 25 show the tenth embodiment of the present invention.
Figure 24:
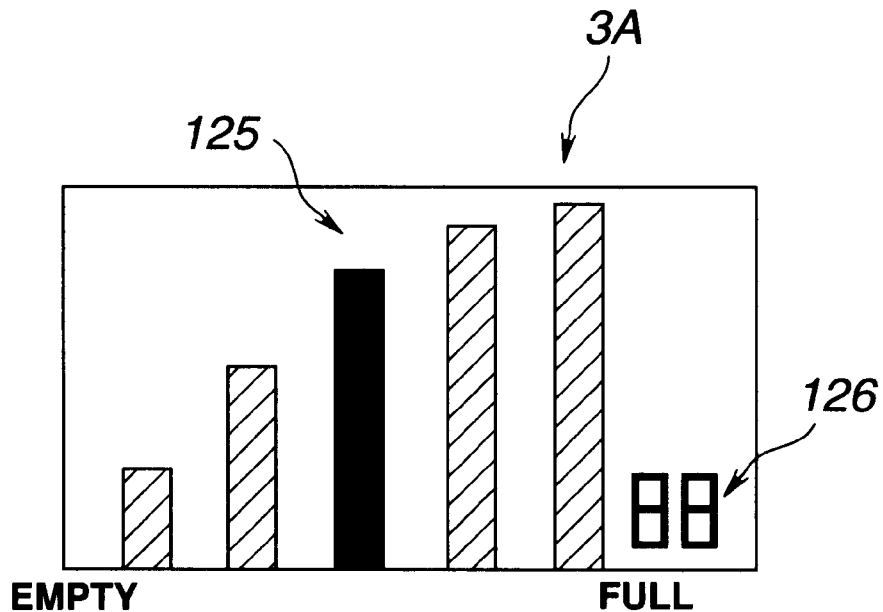

A light source operation circuit in accordance with the present embodiment consists of, as shown in FIG. 23, the battery 5, a counter circuit 121, a voltage detection unit 7*a*, a memory circuit 122, an arithmetic circuit 123, and the liquid crystal panel 3. The battery 5 serves as a power supply for supplying power to the lamp 4. The counter circuit 121 has a lamp lighting detection circuit incorporated therein, and produces a lamp lighting sense signal. The voltage detection unit 7*a* has an A/D converter, which is not shown, incorporated therein, and produces a voltage value signal. The memory circuit 122 includes a recording and holding unit that has the ability to record and hold an integrated time calculated by integrating times during which the lamp 4 is lit using the battery 5, and voltages given by the battery during the times. The memory circuit 122 also produces an integrated lighting time signal that indicates the integrated lamp lighting time and is output together with the voltage value signal. The arithmetic circuit 123 arithmetically detects the exhausted state of a battery from the voltage value signal, and produces a driving signal from the integrated lighting time signal and voltage value signal. The driving signal is used to indicate the estimated remaining usable time of the battery 5 and the usable time of the lamp 4. The liquid crystal panel 3 serves as a remaining battery energy reporting means for indicating an amount of electrical energy contained in a battery in response to the driving signal.

Specifically, an amount of electrical energy contained in a battery and a remaining usable time of the battery or an integrated lighting time of a lamp can be concurrently or selectively indicated as indices indicating the capacity of the battery using the liquid crystal panel of the present embodiment. As shown in FIG. 24, an amount-of-electrical energy indicator 125 and a selected time indicator 126 are defined on the liquid crystal panel 3 of the present embodiment. The selected time indicator 126 can selectively indicate the remaining usable time of the battery or the integrated lighting time of the lamp.

The voltage detection unit 7*a*, arithmetic circuit 123, and liquid crystal panel 3 are electrically connected to one another via the memory circuit 122. The voltage detection unit 7*a*, the counter circuit 121, and the switch 6 used to control the conducting and nonconducting states of the lamp 4 are installed in the middle of a conductive path. Power is always supplied from the battery 5 to the memory circuit 122. The integrated time and battery voltage value are stored and held as memory information in the memory circuit 122. When the battery 5 is replaced with a new one, since power supply is discontinued, the memory information stored and held in the memory circuit 122 is discarded.

Operations to be exerted by the endoscope apparatus having the battery-powered light source that has the foregoing components will be described below.

First, the battery-powered light source of the present embodiment is mounted on the endoscope 1, thus constructing the endoscope apparatus.

Thereafter, the battery-powered light source is driven to conduction, and the lamp 4 is lit. The A/D converter incorporated in the voltage detection unit 7*a* detects a voltage given by a battery, and produces a voltage value signal representing a numerical value that expresses the voltage given by the battery. The voltage value signal is output to the arithmetic circuit 123 via the memory circuit 122.

When the counter circuit 122 senses that the lamp 4 is lit, it produces a lamp lighting sense signal, and outputs the lamp lighting sense signal to the memory circuit 122.

In the memory circuit 122 to which the lamp lighting sense signal is input, a time having elapsed since the lamp 4 started lighting is integrated with the integrated time calculated by integrating times during which the lamp is lit.

The integrated time has been stored in the memory circuit 122. An integrated lighting time signal is then produced and output to the arithmetic circuit 123.

The voltage value and integrated lighting time to be output to the arithmetic circuit 123 are stored and held as new memory information in the memory circuit 122.

The arithmetic circuit 123 executes an arithmetic operation using the input voltage value signal and integrated lighting time signal, and produces a driving signal. The driving signal is output to the liquid crystal panel 3.

Consequently, the remaining usable time of the battery and the amount of electrical energy remaining in the battery are indicated in the form of a bar graph on the liquid crystal panel 3. Instead of indicating the remaining usable time of the battery, the integrated lighting time of the lamp may be indicated so that the remaining usable time of the battery can be inferred from the integrated lighting time.

The switch 6 may be turned off once, and then turned on again. In this case, a re-polarization phenomenon may occur. The re-polarization phenomenon is a phenomenon that apparent electromotive force is restored in the battery 5. The re-polarization phenomenon causes the voltage given by the battery 5 to rise apparently. Therefore, when the voltage value is detected in order to produce a voltage value signal, the amount of electrical energy contained in the battery may be indicated incorrectly.

If the voltage value signal affected by the re-polarization phenomenon is detected, judgment may be made incorrectly. For preventing incorrect judgment, when an amount of electrical energy remaining in a battery is small, the arithmetic circuit 123 starts an arithmetic operation in a delay time so as to cancel the voltage value signal output immediately after the lamp is lit again. During the delay time during which the voltage value signal is canceled, a voltage value signal produced immediately before the switch 6 is turned off previously is output from the memory circuit 122 to the arithmetic circuit 123. The arithmetic operation is carried out based on this voltage value signal. The other components are identical to those of the aforesaid embodiments.

Figure 25:
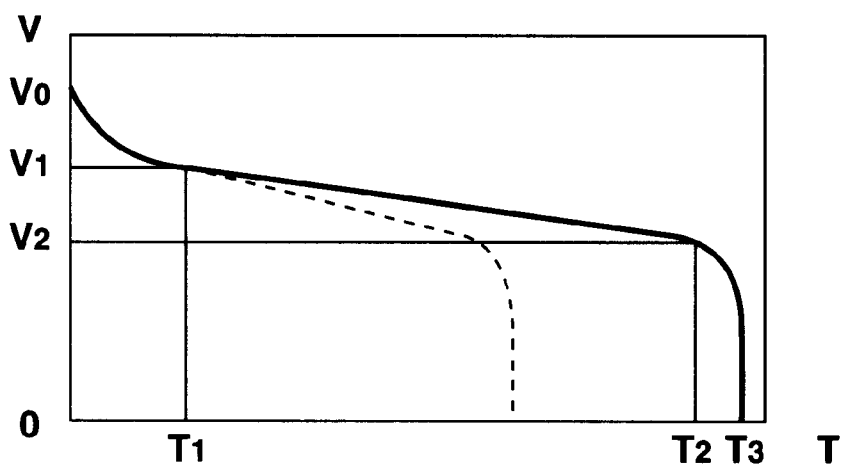

Referring to FIG. 25, the discharge characteristic of a typical battery will be described below.

In the graph of FIG. 25, the axis of ordinates indicates a voltage V, and the axis of abscissas indicates a time instant T. An initial voltage value shall be $V_0$. The value of the voltage having undergone an initial voltage drop shall be $V_1$, and a time instant at the end of the initial voltage drop shall be $T_1$. The value of the voltage having undergone steady-state discharge shall be $V_2$, and a time instant at the end of the steady-state discharge shall be $T_2$. A time instant at which a voltage value of 0 is detected finally shall be $T_3$.

The voltage V undergoing the initial voltage drop, that is, discharge indicated with $0<T<T_1$ and $V_1<V<V_1$ is expressed as the following n-order regression function:

$$V=T^n+T^{n-1}+\ldots+a \quad (1)$$

The voltage undergoing the steady-state discharge, that is, discharge indicated with $T_1<T<T_2$ and $V_2<V<V_1$ is expressed as the following linear repression function:

$$V=Tb+c \quad (2)$$

Moreover, the voltage undergoing discharge that succeeds the steady-state discharge, that is, discharge indicated with $T_2<T<T_3$ and $0<V<V_2$ is expressed as the following m-order regression function:

$$V=T^m+T^{m-1}+\ldots+d \quad (3)$$

Note that a, b, c, d, n, and m in the formulas (1), (2), and (3) denote any constants.

The arithmetic circuit 123 assigns the values represented by the integrated lighting time signal and voltage value signal input from the memory circuit 122 to T and V in the above formulas (1) to (3), and thus calculates a predicted value of a remaining usable time. The arithmetic circuit 123 then produces a driving signal.

Moreover, when the voltage is undergoing the initial voltage drop or any other discharge, the formulas (1) to (3) are solved by adopting predefined values as the constants a, b, c, and d. Moreover, after the voltage has undergone the steady-state discharge, the measured values of V and T are assigned to the formula (2) or (3), and the most likely relationship between V and T is estimated according to, for example, the least squares method. Finally, a predicted value of a remaining usable time is calculated.

Moreover, when a chargeable battery that has not been fully charged or a used battery is employed, after the voltage falls below V1 or V2 according to a curve drawn with a dashed line, the expressions used to calculate a predicted value of a remaining usable time are changed.

As mentioned above, when the lamp incorporated in the battery-powered light source is lit, an amount of electrical energy contained in a battery and the predicted usable time of the battery or the integrated lighting time of the lamp are indicated using the liquid crystal panel. A user is thus informed of the amount of electrical energy contained in the battery and the estimated usable time of the battery.

Moreover, an arithmetic operation is carried out based on the two parameters of the integrated time and battery voltage stored in the memory circuit. The accuracy in the predicted value of the remaining usable time of the battery is improved.

Furthermore, when the remaining usable time of the battery is predicted, the arithmetic circuit is operated in a delay in order to eliminate the re-polarization phenomenon occurring when the switch is turned on again. An amount of electrical energy contained in a battery is therefore indicated more accurately than that in the aforesaid embodiments.

A second battery (not shown) different from the battery 5 may be used as the power supply of the memory circuit 122. Moreover, a second memory circuit may be included aside from the memory circuit 122. An integrated time calculated by integrating times during which the lamp is lit may be stored and held in the second memory circuit. Furthermore, a nonvolatile memory may be used as a storing and holding unit of the memory circuit 122.

Now, the basic circuitry of the voltage detection unit serving as an electrical battery energy detecting means will be described with reference to FIG. 26 and FIG. 27.

Figure 26:
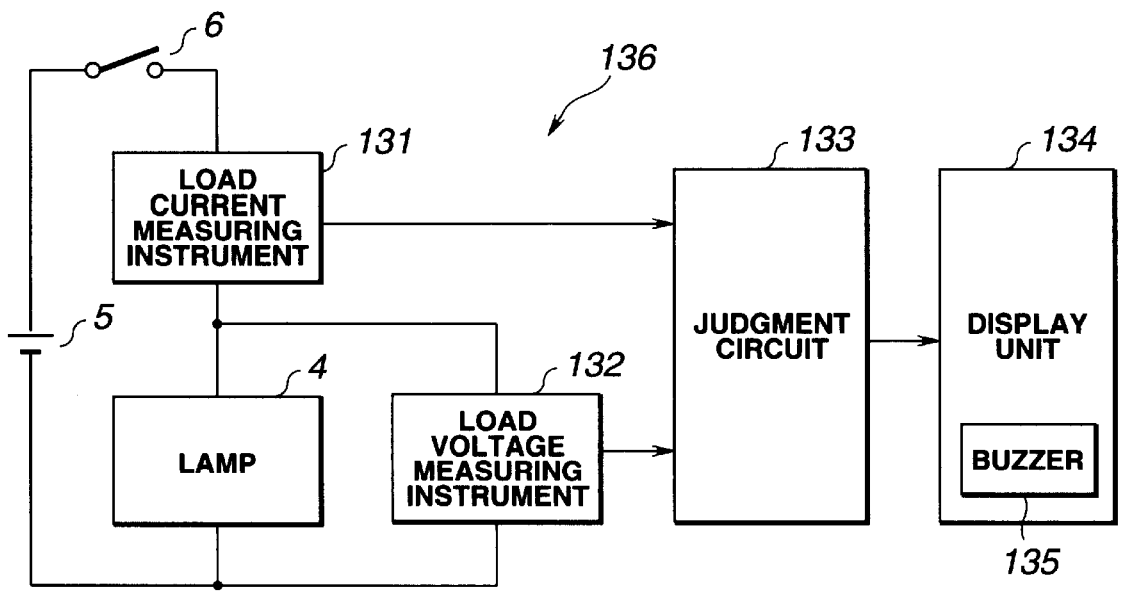
FIG. 26 and FIG. 27 are explanatory diagrams concerning the basic configuration of a voltage detection circuit serving as an electrical battery energy detecting means.

As shown in FIG. 26, a circuit 130 (hereinafter a battery checker) for checking the state of a battery is incorporated in, for example, the battery-powered light source 2. The usable situation of the battery is indicated using an indication unit, which serves as a capacity-of-battery reporting means, formed on the outer circumference of the battery stowage portion 23. Thus, the usable time of the battery can be discerned externally.

The indication unit may be realized with, as mentioned above, a liquid crystal panel for displaying an indicator that simulates a battery and indicates the capacity of a battery as an index. Otherwise, the indication unit may be realized with a level meter composed of a plurality of light-emitting diodes (LEDs) or pilot lamps for indicating a usable time.

The battery checker 130 has the battery 5 connected to the lamp 4, which is regarded as a load, via the switch 6 and a load current measuring instrument 131. A load voltage measuring instrument 132 is connected to the lamp 4. The output terminals of the load voltage measuring instrument 132 and load current measuring instrument 131 are connected to a judgment circuit 133 for calculating and judging the service life of the battery 5 and the remaining usable time thereof. The foregoing indication unit 134 is connected to the output terminal of the judgment circuit 133.

Figure 27:
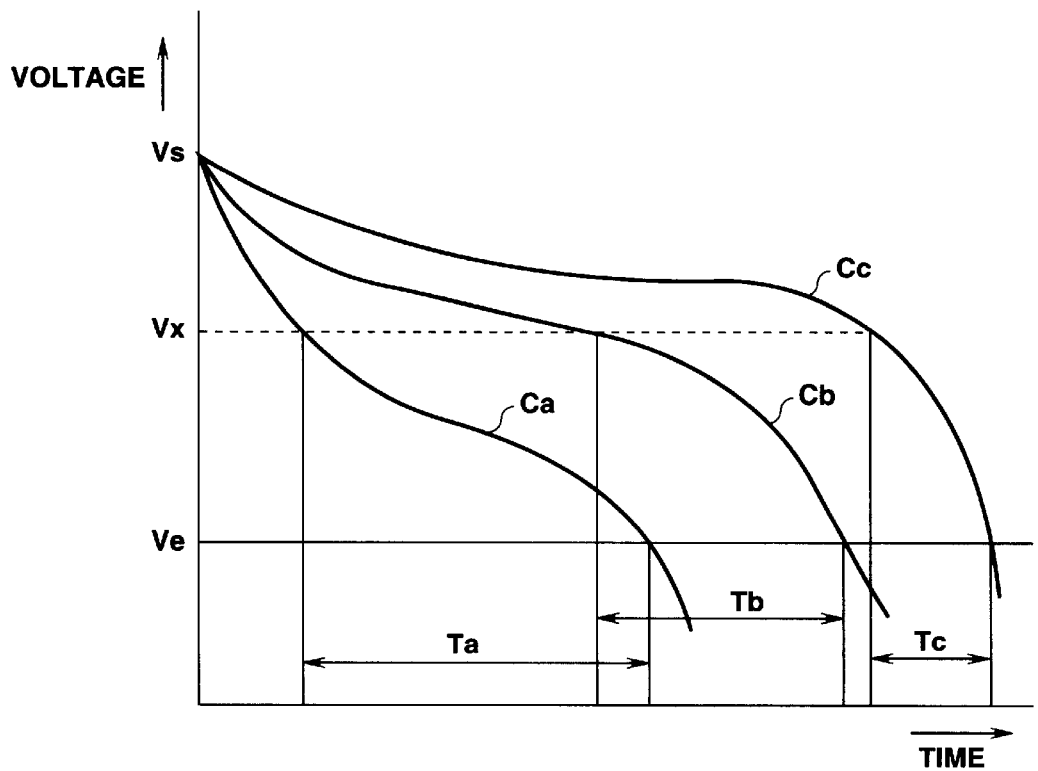

FIG. 27 is a graph showing discharge characteristic curves associated with load currents.

In the graph, curves Ca, Cb, and Cc represent discharge characteristics exhibited by a battery with high, medium, and low loads imposed thereon.

A voltage Vs indicates an initial voltage given by the battery 5, and a voltage Ve is a final voltage of the battery 5. Assuming that a checked voltage is Vx, when the battery exhibits the discharge characteristic represented by the characteristic curve Ca, the usable time of the battery that is the time elapsed until the voltage Vx falls down to the final voltage Ve is Ta.

Likewise, when the battery exhibits the discharge characteristics represented by the characteristic curves Cb and Cc, the usable times of the battery are Tb and Tc. Consequently, the remaining usable time of a battery elapsing can be retrieved based on the checked voltage Vx from the graph of the discharge characteristic curves.

In the battery checker 130, the judgment circuit 133 calculates the usable time of a battery. When the switch 6 is turned on, the load current measuring instrument 131 measures a current flowing into the lamp 4.

The measured load current is supplied together with a load voltage measured by the load voltage measuring instrument 132 to the judgment circuit 133. The judgment circuit 133 selects any of the discharge characteristic curves according to the measured load current flowing into the lamp 4.

The usable time of the battery is calculated based on the selected discharge characteristic curve and measured load voltage. The output information of the judgment circuit 133 is supplied to the indication unit 134, whereby the usable time is indicated.

Moreover, an alarm, for example, a buzzer 135 is included in the indication unit 134. The buzzer 135 sounds when a calculated usable time is short or nil, and thus reports the fact to a user.

As mentioned above, according to the present embodiment, the usable time of the battery 5 is calculated based on a discharge characteristic curve associated with a load current and a checked load voltage. The usable time is indicated using the indication unit 134.

Consequently, when the amount of electrical energy contained in the battery 5 is checked using the battery checker 130 prior to a surgical procedure, it can be judged whether electrical energy permitting the use of the battery-powered light source is still available. An event that the battery 5 is exhausted in the course of observation can be avoided.

Figure 28:
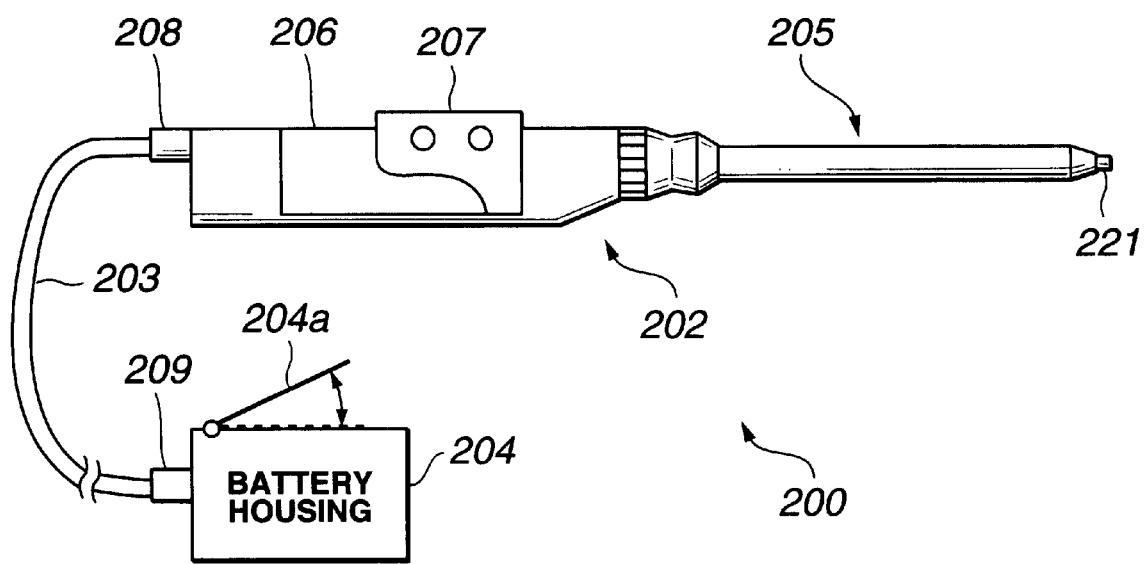
FIG. 28 and FIG. 29 show the eleventh embodiment of the present invention.
Figure 29:
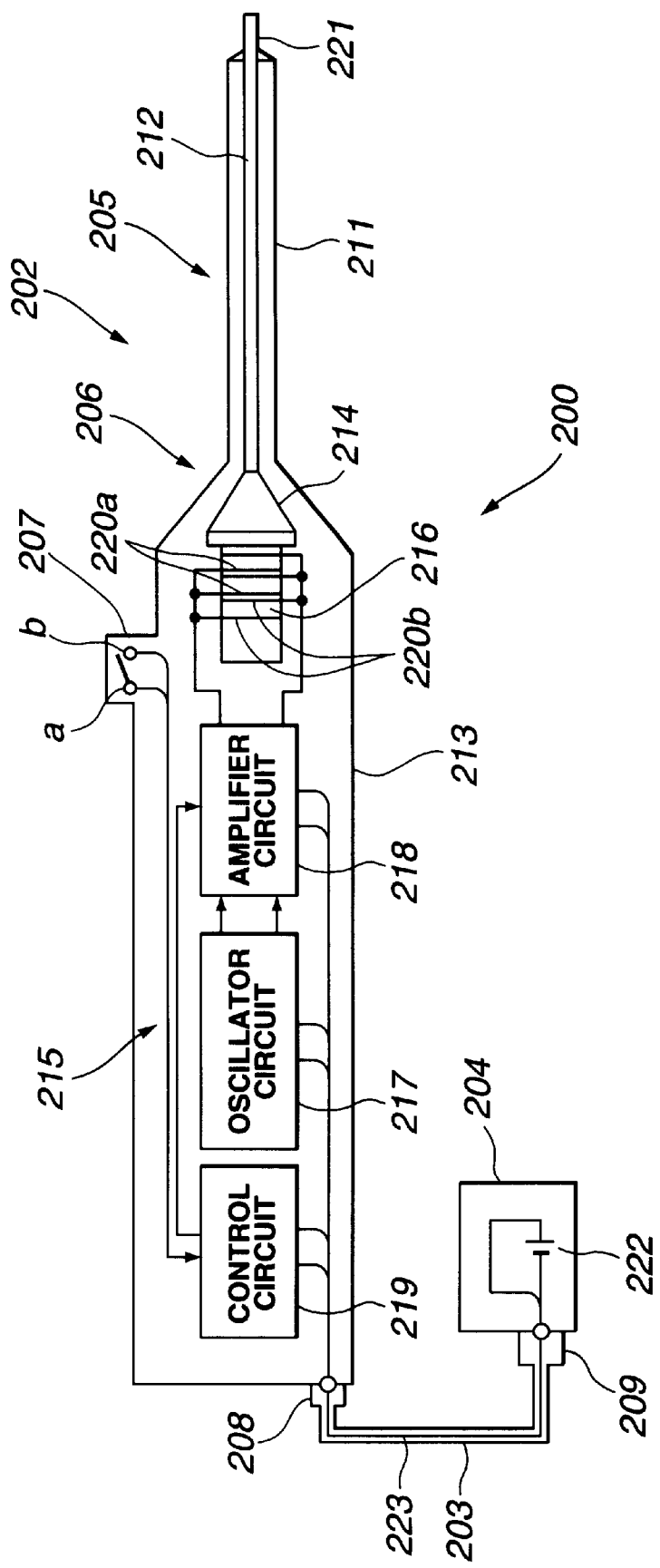

Referring to FIG. 28 and FIG. 29, the eleventh embodiment of the present invention will be described below.

As shown in FIG. 28, an operation apparatus of the present embodiment is an ultrasonic operation apparatus 200 consisting of a main body 202, a flexible cord (or flexible tube) 203, and a battery housing 204. The main body 202 is a surgical instrument used to perform surgery ultrasonically. The flexible cord 203 is linked to the main body 202. The battery housing 204 is freely detachably attached to the other end of the flexible cord 203.

The main body 202 has an insertion portion 205 to be inserted into a body cavity and a hand piece unit 206 united with the proximal end in an axial direction of the insertion portion 205. The hand piece unit 206 is a hand-held control section held by an operator for performing manipulations. A switch unit 207 to be turned on or off in order to enable or disable a treatment is mounted on the hand piece unit 206.

A connector 208 attached to one end of the flexible cord 203 is coupled to the back end of the hand piece unit 206 so that the connector 208 can be freely uncoupled. A connector 209 attached to the other end of the flexible cord 203 is coupled to the battery housing 204 so that the connector 209 can be uncoupled freely.

As shown in FIG. 29, the insertion portion 205 has a probe 212 passed through a sheath 211 thereof. The back end of the probe 212 is coupled to an ultrasonic transducer 216 included in a drive unit 215 via a horn 214 incorporated in a housing 213 of the hand piece unit 206. The ultrasonic transducer 216 is realized with, for example, a bolted Langevin ultrasonic transducer.

The housing 213 accommodates an oscillator circuit 217 serving as an oscillator for generating a high-frequency signal of a frequency f1 that is the resonant frequency shared by the ultrasonic transducer 216 and probe 212. The housing 213 also accommodates an amplifier circuit 218 serving as a power amplifying means for amplifying in power an oscillatory signal output from the oscillator circuit 217 and outputting a driving signal, and a control circuit 219 for controlling the amplifier circuit 218.

The output signal of the amplifier circuit 218 is applied to electrodes 220a and 220b included in the ultrasonic transducer 216.

When the switch unit 207 is turned on or off in order to link or unlink contacts a and b, a signal is input to the control circuit 219. The control circuit 219 activates or inactivates the amplifier circuit 218 so as to control output of a driving signal to the ultrasonic transducer 216.

To be more specific, when the switch unit 207 is turned on, an oscillatory signal output at the frequency f1 from the oscillator circuit 217 is input to the amplifier circuit 218 by means of the control circuit 219. The oscillatory signal is amplified and then supplied to the ultrasonic transducer 216. The ultrasonic transducer 216 is then driven, whereby oscillations produced at the resonant frequency f1 are conveyed to the probe 212. When a treatment portion 221 that is the distal part of the probe 212 is brought into contact with or pressed against a lesion, treatment for cure, for example, incision can be carried out.

A battery 22 is stowed in the battery housing 204. The battery 222 supplies action power or power required for actions to the control circuit 219, oscillator circuit 217, and amplifier circuit 218 over a flexible power supply line 223 lying through the flexible cord 203.

When electrical energy in the battery 222 runs out, a lid 204a of the battery housing 204 through which a battery is replaced with a new one is turned from a position indicated with a dashed line in FIG. 28 to a position indicated with a solid line. The exhausted battery 22 can be readily replaced with a new one 222.

The flexible cord 203 has a length making it possible to place the battery housing 204 on a patient's body or a patient couch while an operator is holding the hand piece unit 206. Even when the operator holds the hand piece unit 206, he/she will not find the battery housing 204 heavy but can proceed with surgery.

When a sheet-type battery is used or the battery 222 is lightweight, while the hand piece unit 206 is being held, the battery housing 204 may float or hang freely.

In the ultrasonic operation apparatus 200 of the present embodiment, no battery is incorporated in the main body 202 held by an operator for performing treatment such as incision. The battery 122 is stowed in the battery housing 204 coupled to the flexible cord 203 extending from the main body 202. Consequently, the main body 202 whose insertion portion 205 and hand piece unit 206 are used to perform treatment is lightweight. This leads to improved maneuverability. Moreover, treatment can be achieved with high precision. Even when it takes much time to complete a treatment, the fatigue an operator feels will be light.

Moreover, when electrical energy in the battery 222 has run out, the main body 202 need not be touched but the lid 204a of the battery housing 204 is opened. Thus, the battery 222 can be replaced with a new one quickly and easily. This leads to improved maneuverability. In this case, a paramedic can replace the battery 222 with a new one on behalf of an operator. Even when surgery is under way, a time during which the surgery is interrupted can be minimized.

Moreover, if electrical energy in the battery 222 runs out, the battery 222 may not be replaced with a new one by opening the lid 204a. Instead, the battery housing 204 that can be freely coupled to or uncoupled from the flexible cord 203 by attaching or detaching the connector 9 may be replaced with another battery housing 204 in which a new battery is stowed. Even in this case, the main body 202 need not be touched for replacement.

The battery 222 may be realized with a chargeable secondary battery or a primary battery that is not chargeable.

Figure 30:
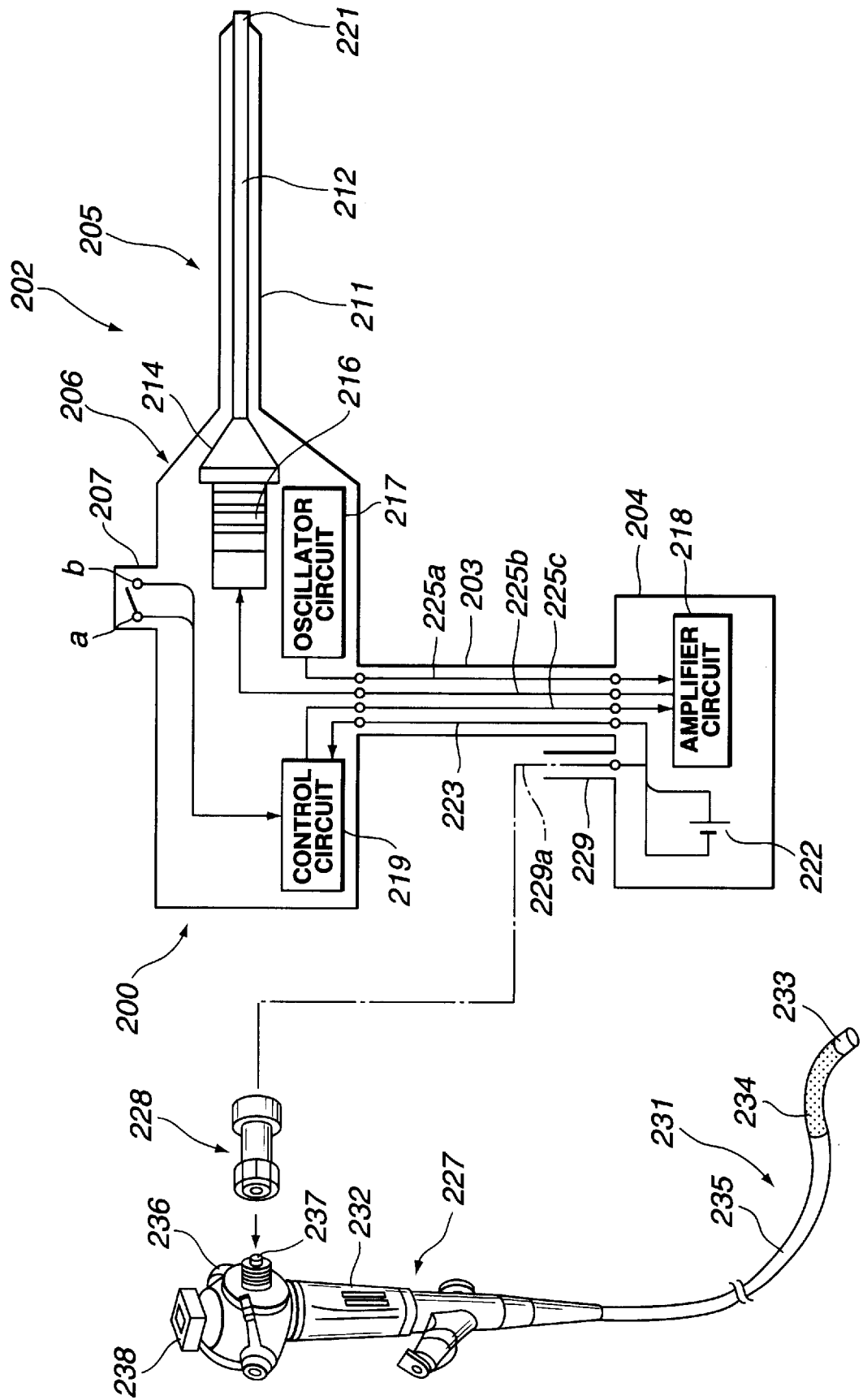
FIG. 30 shows the configuration of an electric system included in an ultrasonic operation apparatus in accordance with the twelfth embodiment of the present invention.

The twelfth embodiment will be described with reference to FIG. 30.

In an ultrasonic operation apparatus 200 of the present embodiment, some of components of the drive unit 215 incorporated in the hand piece unit 206 shown in FIG. 29 are incorporated in the battery housing 204. The same reference numerals are assigned to components identical to those of the eleventh embodiment.

The ultrasonic transducer 216, oscillator circuit 217, and control circuit 219 constituting the driving means and incorporated in the hand piece unit 206 are identical to those of the eleventh embodiment. The description of these components will therefore be omitted.

Among the components of the driving means, the amplifier circuit 218 occupies a wide area or is heavy. In the present embodiment, the amplifier circuit 218 is incorporated in the battery housing 204. The battery 222 is connected to the control circuit 219 in the hand piece unit 206 over a power supply line 223 lying through the flexible cord 203. In FIG. 30, for brevity's sake, the power supply line 223 is connected to the control circuit 219 alone.

Moreover, an output signal of the oscillator circuit 217 is input to the amplifier circuit 218 in the battery housing 204 over a signal line 225a passing through the flexible cord 203. An output signal of the amplifier circuit 218 is supplied to the ultrasonic transducer 216 over a signal line 225b passing through the flexible cord 203. The control circuit 219 is connected to the amplifier circuit 218 over a signal line 225c passing through the flexible cord 203. The control circuit 219 controls amplification.

According to the present embodiment, the main body 202 can be designed to be more lightweight and compact than that in the eleventh embodiment. This leads to further improved maneuverability. The other operations and advantages are identical to those of the eleventh embodiment.

In the eleventh embodiment, the amplifier circuit 218 is incorporated in the hand piece unit 206. Since the battery 222 is not incorporated in the hand piece unit, the hand piece unit 206 is lightweight. By contrast, when the amplifier circuit 218 is not incorporated in the hand piece unit 206, the hand piece unit 206 can be designed to be more compact and lightweight. This leads to smoothened surgery.

In the present embodiment, a lamp housing 228 is freely detachably attached to a battery-powered endoscope having a light source driven with a battery, for example, an electronic endoscope (video scope) 227. A light source lamp (illumination lamp), which is not shown, incorporated in the lamp housing 228 is connected to the battery 222 over a cable 229a lying through a flexible cord 229. Power is thus supplied from one battery housing 204 to a plurality of devices.

In short, the battery 222 in the battery housing 204 supplies power required for lighting the light source lamp in the battery-powered endoscope.

The electronic endoscope 227 has an elongated insertion portion 231, and a control section 232 attached to the back end of the insertion portion 231. The insertion portion 231 consists of a distal part 233, a bending section 234, and a flexible part 235. The bending section 234 can be angled properly by manipulating an angling knob 236 formed on the control section 232.

The back end of a light guide, which is not shown, lying through the insertion portion 231 is jutted out from the flank of the control section 232 and formed as a light guide base 237. The lamp housing 228 in which the light source lamp is stowed can be coupled to the light guide base 237 so that the lamp housing 228 can be uncoupled freely. When the light source lamp is lit, a lesion can be illuminated by way of the light guide.

An optical image is projected on an imaging device located on the image plane of an objective lens, which is not shown, incorporated in the distal part 233. An electrical signal to which the optical image is transformed is processed by a signal processing circuit, which is not shown, incorporated in the control section 232. Consequently, a produced object image is displayed on a display device 238 such as a liquid crystal display device located on the back end of the control section 232.

Conventionally, a plurality of battery housings is placed on a patient's body or a patient couch. According to the present invention, the battery housing 204 alone is placed thereon. An operator will therefore not be bothered with the plurality of battery housings.

Figure 31:
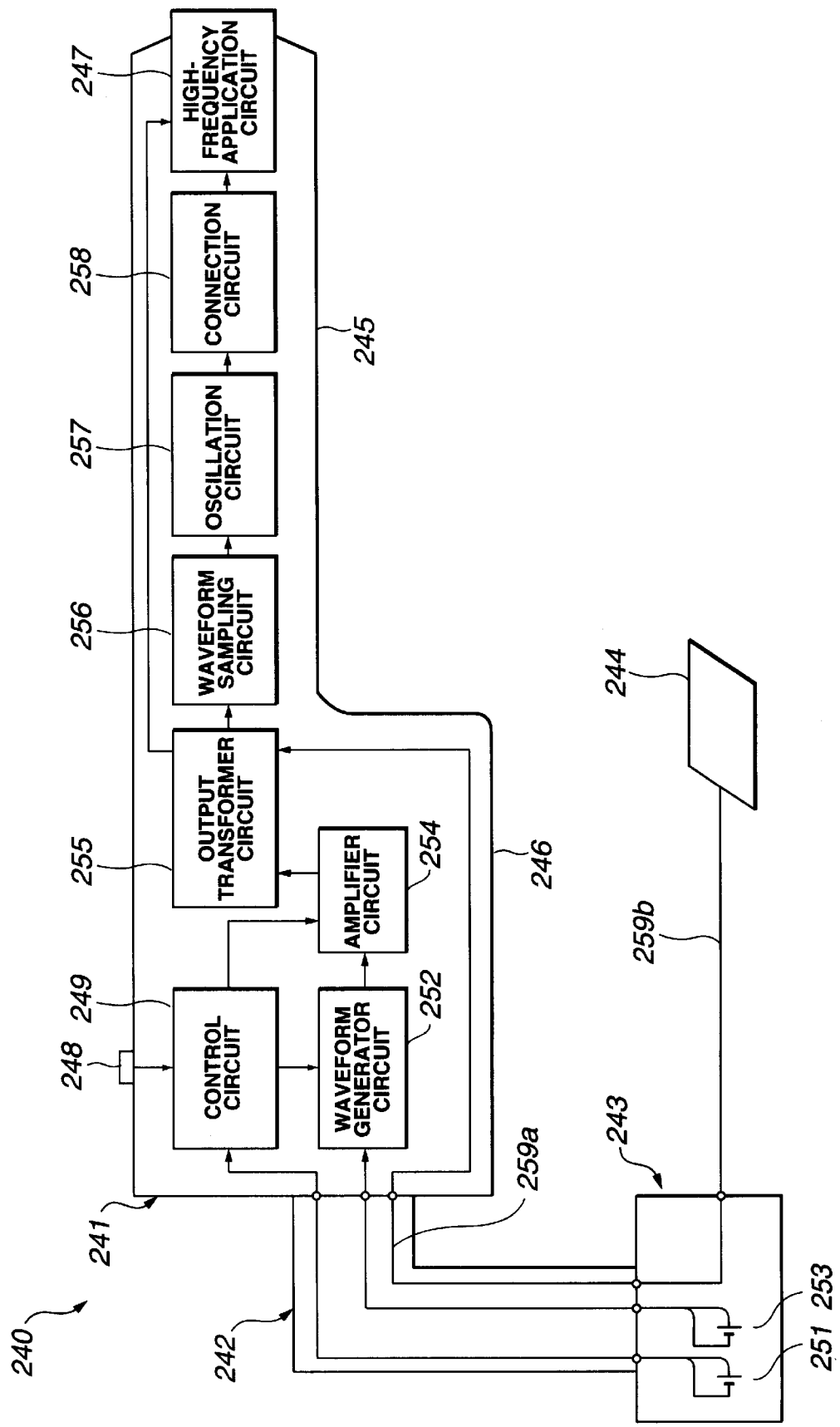
FIG. 31 shows the configuration of an electric system included in a high-frequency operation apparatus in accordance with the thirteenth embodiment of the present invention.

The thirteenth embodiment of the present invention will be described with reference to FIG. 31.

As illustrated, a high-frequency operation apparatus 240 that is an operation apparatus of the present embodiment and has a surgical instrument consists of a hand piece 241, a battery housing 243, and a counter-electrode plate 244. The hand piece 241 outputs high-frequency electrical energy required for electrically performing surgery to a living body. The battery housing 243 is connected to the hand piece 241 over a flexible tube 242 extending outward from the hand piece 241. The counter-electrode plate 244 connected to the battery housing 243 collects high-frequency electrical energy output to the living body.

An insertion portion 245 to be inserted into a body cavity is united with the front end of the hand piece 241. A control section 246 held for performing manipulations is united with the back end of the hand piece 241.

A high-frequency application unit 247 for outputting high-frequency electrical energy to a patient's living body for electrical treatment is incorporated in the distal part of the insertion portion 245. A switch 248 to be turned on or off for enabling or disabling output of high-frequency electrical energy is formed on the control section 246.

A battery 251 and a battery 253 are incorporated in the battery housing 243 connected to the hand piece 241 over the flexible tube 242 extending outward from the hand piece. The battery 251 supplies power required for driving a control circuit 249 included in a driving means incorporated in the control section 246. The battery 253 supplies power required for driving a waveform generator circuit 252 incorporated in the control section 246.

The waveform generator circuit 252 generates a high-frequency driving signal used to perform high-frequency surgery. The driving signal is a high-frequency signal having a mechanical oscillation frequency component that brings about mechanical oscillations. The frequency component has a low frequency that is a fifth or sixth to about tenth part of the frequency of a high-frequency signal used for high-frequency treatment.

The driving signal is input to the amplifier circuit 254, and then input to a primary winding of an output transformer circuit 255 whose input and output terminals are isolated from each other. The isolated secondary winding thereof is connected to a waveform sampling circuit 256 and the counter-electrode plate 244.

Action power is supplied from the battery 251 to the control circuit 249 that controls actions of the waveform generator circuit 252 and amplifier circuit 254.

The control circuit 249 is connected to the switch 248. When a manipulation signal produced by manipulating the switch 248 is input to the control circuit, the control circuit 249 activates or inactivates the waveform generator circuit 252 and the amplifier circuit 254. The control circuit 249 thus enables or disables output of high-frequency electrical energy. Otherwise, the control circuit 249 may enable or disable power supply so as to prevent supply of power from the battery 253 to the waveform generator circuit 252 due to a manipulation performed on the switch 248. The control circuit 249 may thus enable or disable output of high-frequency electrical energy.

An output provided through one output terminal of the secondary winding of the output transformer circuit 255 is applied to the waveform sampling circuit 256 for sampling a mechanical oscillation frequency component and the high-frequency application unit 247 with which treatment such as resection is performed using high-frequency current.

Moreover, an output of the waveform sampling circuit 246, that is, a mechanical oscillation frequency component is applied to an oscillation circuit 257 that transforms it into oscillatory energy. Namely, the oscillation circuit 257 is oscillated. The oscillations are conveyed to the high-frequency application unit 247 via a connection circuit 258 for conveying oscillations from the oscillation circuit 257 to the high-frequency application unit 247. The high-frequency application unit 247 is oscillated, whereby a living tissue with which the high-frequency application unit 247 is in contact is resected or coagulated or undergoes any other electric treatment.

The other output terminal of the secondary winding of the output transformer circuit 255 is connected to the counter-electrode plate 244 via the battery housing 243. Specifically, the other output terminal of the output transformer circuit 255 is connected to the counter-electrode plate 244 over a signal line 259a lying through the flexible tube 242 and a signal line 259b linked to the battery housing 243.

Consequently, high-frequency current flows into a patient's tissue with which the high-frequency application unit 247 incorporated in the distal part of the hand piece 241 is in contact. The current is then returned to the output transformer circuit 255 via the counter-electrode plate 244 placed in contact with the patient by a large area. Thus, a closed loop is set up.

The present embodiment is a high-frequency operation apparatus having a mono-polar electric cautery.

The flexible tube 242 has the same operation and advantage as that in the eleventh or twelfth embodiment. The present embodiment provides the same advantages as the eleventh embodiment.

Figure 32:
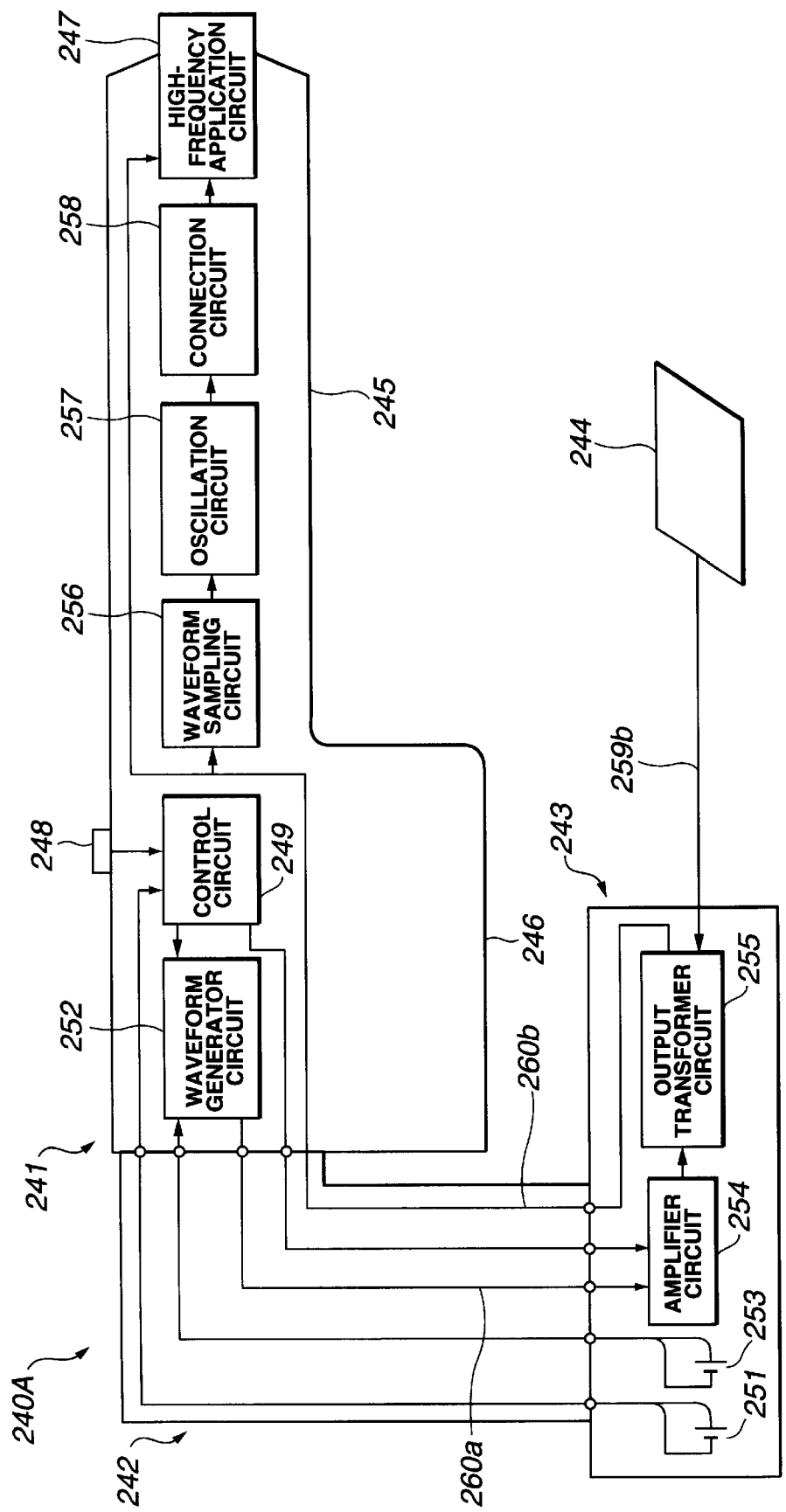
FIG. 32 shows the configuration of an electric system included in a high-frequency operation apparatus in accordance with the fourteenth embodiment of the present invention.

The fourteenth embodiment of the present invention will be described with reference to FIG. 32.

A high-frequency operation apparatus 240A of the present embodiment is a variant of the thirteenth embodiment and has the same circuitry as the thirteenth embodiment.

In the circuitry of the thirteenth embodiment, the amplifier circuit 254 and output transformer circuit 255 occupy relatively large spaces. When these circuits are incorporated in the hand piece 241, the hand piece 241 becomes heavy. This leads to a burden an operator must incur during surgery.

According to the present embodiment, the amplifier circuit 254 and output transformer circuit 255 are incorporated in the battery housing 243. The weight of the hand piece 251 is thus lightened.

An output signal of the waveform generator circuit 252 is input to the amplifier circuit 254 in the battery housing 243 over a signal line 260 passing through the flexible tube 242. An output signal of the amplifier circuit 254 is input to the output transformer circuit 255.

A driving signal output through one output terminal of the output transformer circuit 255 is applied to the waveform sampling circuit 256 and high-frequency application unit 247 incorporated in the hand piece 241 over a signal line 260b passing through the flexible tube 242.

Moreover, a high-frequency signal provided from the high-frequency application unit 247 and passed through a living tissue is collected by the counter-electrode plate 244 and returned to the output transformer circuit 255 over a signal line 259b.

According to the present embodiment, the control section 246 can be designed to be more compact and lightweight than that in the thirteenth embodiment. This leads to further improved maneuverability.

The fifteenth embodiment of the present invention will be described with reference to FIG. 33.

As illustrated, an ultrasonic cure device 261 that is a surgical instrument included in an operation apparatus of the present embodiment consists of a hand piece 262 and a battery housing 265 in which a battery 264 is stowed. A flexible cord 263 extending from the hand piece 262 is linked to the battery 264.

The hand piece 262 is used in combination with an ultrasonic coagulation/resection device having a forceps-like probe for coagulating or resecting a lesion by utilizing heat that stems from ultrasonic oscillations. The hand piece 262 has a hand-held unit 266 in which an ultrasonic transducer is incorporated, and a sheath 267 which communicates with the front end of the hand-held unit 266 and in which an ultrasonic oscillation conveyance member is incorporated. A flexible cord 263 over which power is supplied to the ultrasonic transducer and which is linked to the battery housing 265 is extending from a connector portion 269 attached to the back end of the hand-held unit 266.

A horn that is not shown is interposed between the ultrasonic transducer and oscillation conveyance member. The horn mechanically amplifies ultrasonic oscillations produced by the ultrasonic transducer and conveys them to the oscillation conveyance member. Moreover, the tip of the sheath 267 is held open. A jaw 271 that can pivot freely and the oscillation conveyance member 272 are jutting out of the tip of the sheath 267.

The jaw 271 can pivot freely with an axis of rotation, which is not shown, as a center. The jaw 271 is caused to pivot, thus clamping a lesion in cooperation with the oscillation conveyance member 272.

The jaw 271 is mechanically coupled to a handle 273 attached to the hand-held unit 266 by way of a coupling wire or the like lying through the sheath 267. The jaw 271 can be caused to pivot by moving the handle 273 in directions of arrows in the drawing. In other words, a forceps-like structure composed of the jaw 271 and oscillation conveyance member 272 can be opened or closed as indicated with arrows.

Incidentally, a switch is incorporated in the hand-held unit 266. The switch is turned on when a rotor portion of the handle 273 is moved in a direction of approaching a stator thereof. The switch is turned off when the rotor is moved in a direction of receding from the stator. With an output of the switch, ultrasonic oscillations produced by the ultrasonic transducer are conveyed to the oscillation conveyance member 272, which is the distal part of the hand piece, via a control circuit that is not show. Consequently, a lesion or the like clamped by the oscillation conveyance member 272 and jaw 271 is coagulated or incised.

The jaw 271 is made of a soft material such as Teflon or a metal. The flexible cord 263 provides the same operation and advantage as that in any of the eleventh to thirteenth embodiments. The present embodiment provides the same advantages as the eleventh embodiment.

Figure 33:
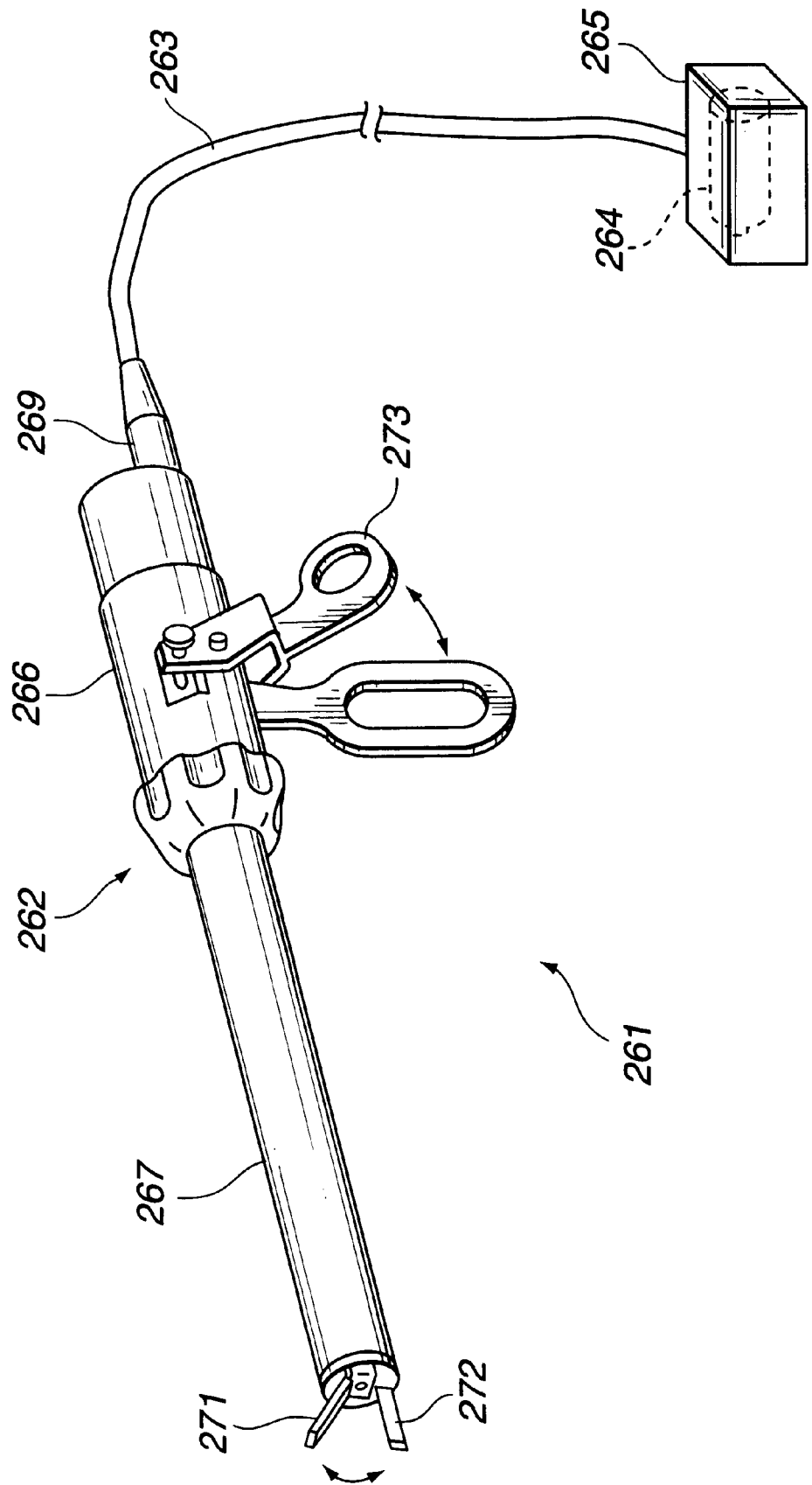
FIG. 33 shows the overall configuration of an ultrasonic cure device in accordance with the fifteenth embodiment of the present invention.
Figure 34:
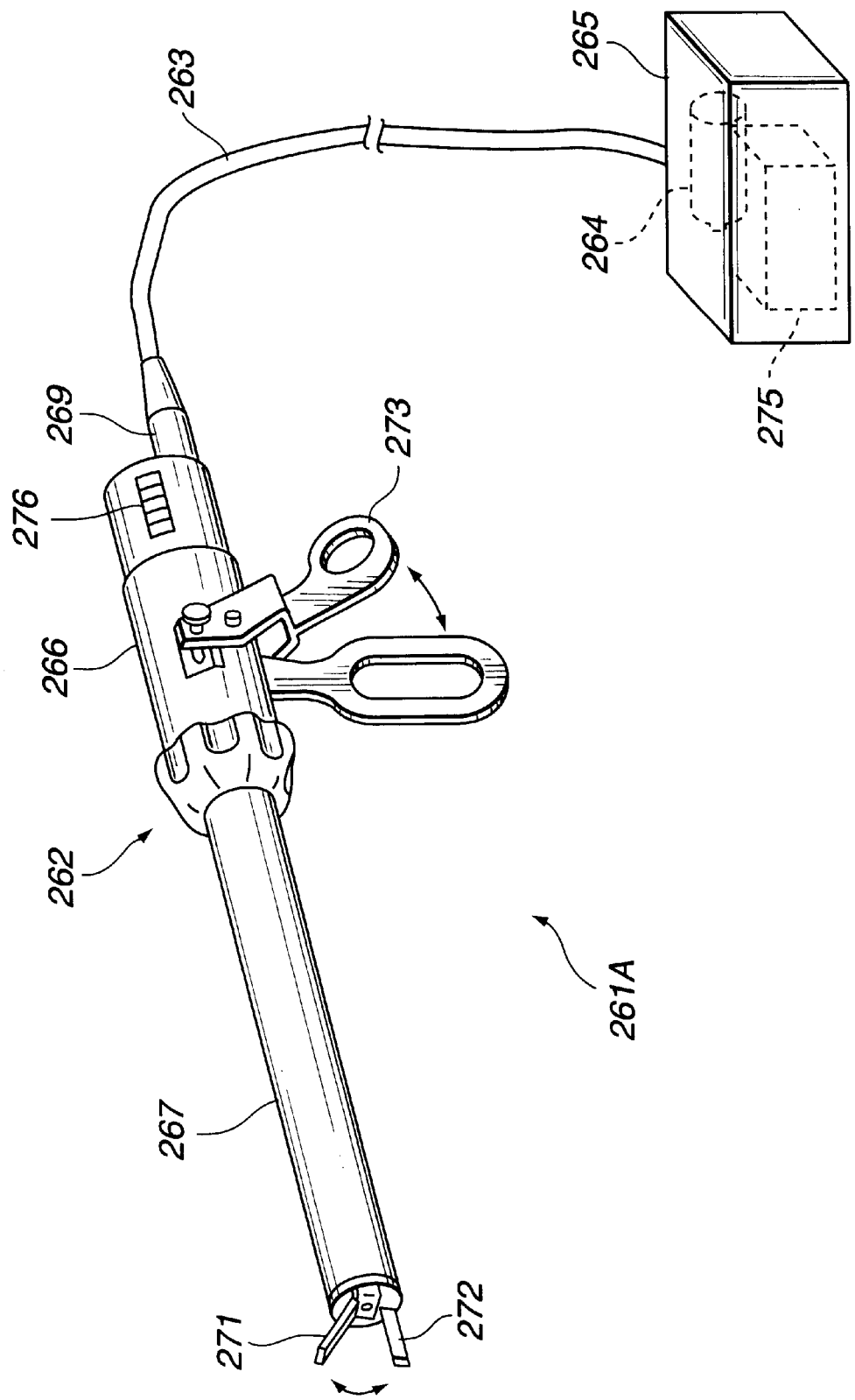
FIG. 34 is an oblique view showing an applied example of ultrasonic cure devices in which the present invention is implemented.

As shown in FIG. 34, an ultrasonic cure device 261A has, in addition to the same components as those of the ultrasonic cure device 261 shown in FIG. 33, a battery checker 136 incorporated in the battery housing 265. The battery checker 136 has the ability to check how long the battery 264 is usable. An indicator 276 for indicating the result of judgment made by the battery checker 136 is mounted on the outer circumference of the hand-held unit 266. A usable time by which the battery 264 is usable is indicated on the indicator 276, so that the usable time can be discerned easily externally.

The indicator 276 may be formed as a level meter indicating a usable time as a level indicated with a meter. Alternatively, the indicator 276 may be formed with a plurality of LEDs or pilot lamps, wherein the usable time is indicated with how many LEDs are lit. In the present embodiment, the ultrasonic cure device 261A is a load but the lamp 4 is not.

The usable time of the battery 264 is calculated based on information of a discharge characteristic curve relative to a load current and a load voltage detected during checking. The usable time is indicated with the indicator 276. When surgery is under way using battery-powered medical equipment, for example, the ultrasonic cure device 261A, it will not take place that surgery is suspended because the battery 264 is exhausted in the course of surgery.

Specifically, the battery checker 275 checks the capacity of the battery prior to surgery. The amount of electrical energy contained in the battery 264 is thus checked to see if electrical energy needed to complete surgery remains. The incident that the battery 264 is exhausted in the course of surgery can be avoided. In the present embodiment, the battery checker 265 is incorporated in the battery housing 265. Alternatively, the battery checker 265 may be incorporated in the hand-held unit 266. Otherwise, the battery 264 may be incorporated in the ultrasonic cure device that is a load. Moreover, the location of the indicator 276 is not limited to the hand-held unit 266. Alternatively, the indicator 276 may be mounted on the battery housing 265.

Figure 35:
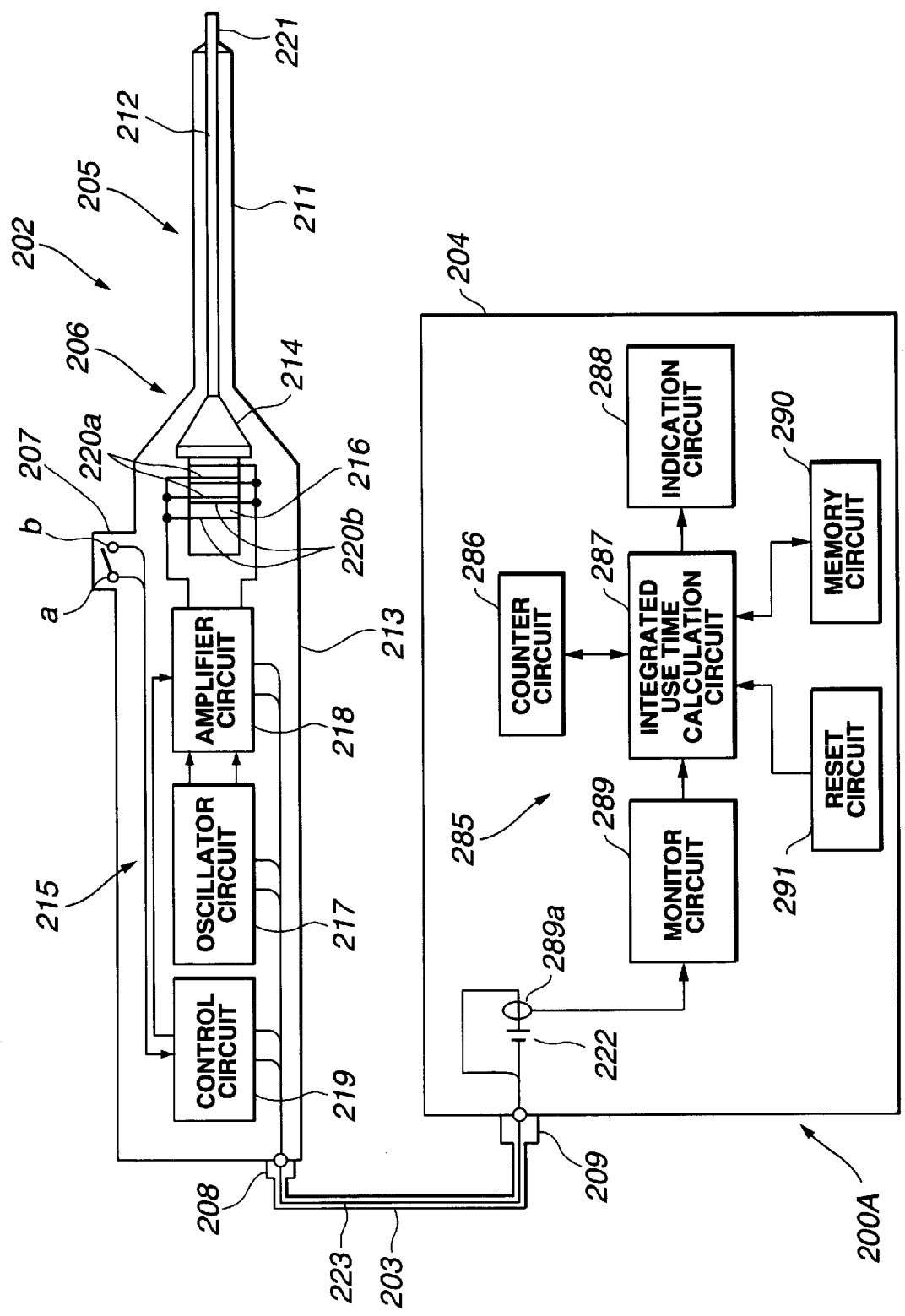
FIG. 35 shows the configuration of an electric system included in an ultrasonic cure device in accordance with the sixteenth embodiment of the present invention.

The sixteenth embodiment of the present invention will be described with reference to FIG. 35.

As illustrated, an ultrasonic operation apparatus 200A that is an operation apparatus of the present embodiment has, in addition to the same components as those of, for example, the ultrasonic operation apparatus 200 shown in FIG. 28, a battery checker 285 incorporated in the battery housing 204. The description of components identical to those of the eleventh embodiment will be omitted.

As illustrated, the battery checker 285 consists of the battery 222, a counter circuit 286, a integrated use time calculation circuit 287, an indication circuit 288, a monitor circuit 289, a nonvolatile memory circuit 290, and a reset circuit 291. The counter circuit 286 measures a use time by which the battery 222 has been used. The integrated use time calculation circuit 287 integrates use times measured by the counter circuit 286. The monitor circuit 289 monitors use of the battery 222. An integrated use time is stored in the nonvolatile memory circuit 290. The reset circuit 291 resets the data of the integrated use time stored in the memory circuit 290.

Based on an output of a current sensor 289a for detecting whether current has flowed into the battery 222, the monitor circuit 289 detects whether electrical energy contained in the battery 222 has been consumed. The monitor circuit 289 outputs a signal, which indicates that the battery 222 is in use, to the integrated use time calculation circuit 287.

When the battery 222 is used, the integrated use time calculation circuit 287 reads data of an integrated use time from the memory circuit 290. While receiving a signal, which indicates that power contained in the battery 222 is consumed, from the monitor circuit 289, the integrated use time calculation circuit 287 instructs the counter circuit 286 to measure a use time.

The integrated use time calculation circuit 287 calculates an integrated use time from the data of the integrated use time read from the memory circuit 290 and the use time measured by the counter circuit 286. The integrated use time calculation circuit 287 then instructs the indication circuit 288 to indicate the integrated use time.

When power supply from the battery 222 is stopped, the monitor circuit 289 sends a signal indicating the fact to the integrated use time calculation circuit 287. An integrated use time calculated at the time when power supply is stopped is stored in the memory circuit 290.

When the battery 222 is replaced with a new one, the reset circuit 291 is activated. A signal indicating the fact is then sent to the integrated use time calculation circuit 287. The integrated use time stored in the memory circuit 290 is then reset to zero.

As mentioned above, according to the present embodiment, it is possible to check the state of the battery 222, that is, the amount of electrical energy. Occurrence of such an incident that the battery 22 must be replaced with a new one during surgery because electrical energy contained in the battery 222 runs out can be avoided.

Figure 36:
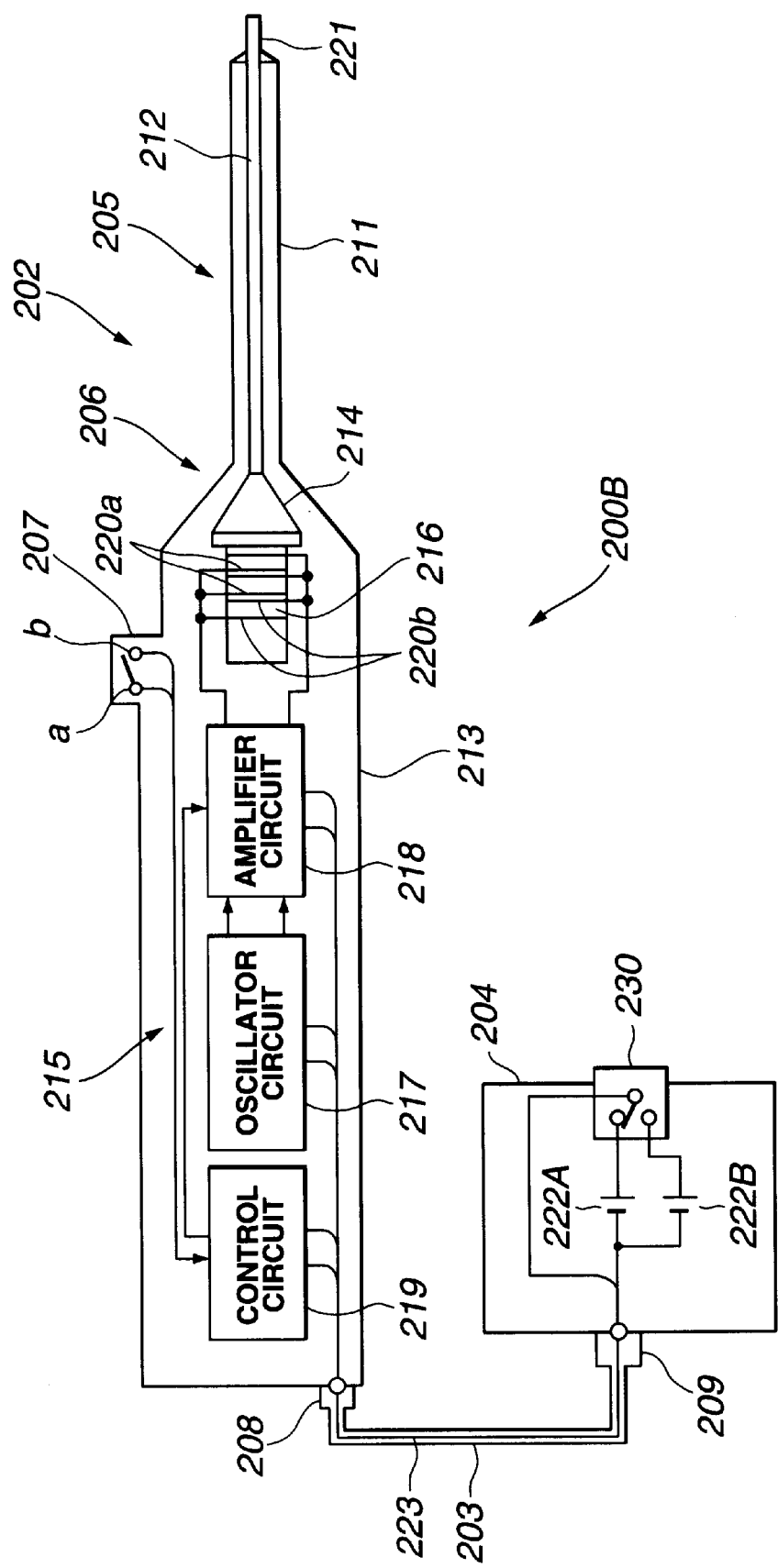
FIG. 36 shows the configuration of an electric system included in an ultrasonic cure device in accordance with the seventeenth embodiment of the present invention.

The seventeenth embodiment of the present invention will be described with reference to FIG. 36.

An operation apparatus of the present embodiment is an ultrasonic operation apparatus 200B. The ultrasonic operation apparatus 200B has the same components as those of, for example, the eleventh embodiment except that the battery 222 in the battery housing 204 is composed of a main battery 222A and a sub battery 222B and that a selection switch 230 is included. By manipulating the selection switch 230, a state in which electrical energy is supplied from the main battery 222A to the electric circuits in the drive unit 215 can be switched to a state in which electrical energy is supplied from the sub battery 222B thereto, or vice versa.

Owing to this configuration, for example, when electrical energy in the main battery 222A runs out during surgery, the selection switch 230 is manipulated for supplying electrical energy used to drive the drive unit 215 from the sub battery 222B. Consequently, surgery can be continued without suspension. The other operations and advantages are identical to those of the eleventh embodiment.

In the present embodiment, the selection switch 230 is mounted on the battery housing 204. Alternatively, the selection switch 230 may be mounted on the hand piece unit 206 or any other position on the main body 202 at which the selection switch can be manipulated easily. Moreover, the selection switch can be adapted to an ultrasonic operation apparatus having the main battery 222A and sub battery 22B incorporated in the hand piece unit 206 or any other place in the main body 202.

Moreover, the battery checker 285 or the like may be used to check the state of the main battery 222A or sub battery 222B connected to the drive unit 215, that is, the amount of electrical energy remaining in the main battery 222A or sub battery 222B. In this case, when the amount of electrical energy diminishes, one battery may be automatically switched to the other according to judgment made by the battery checker 285.

The eighteenth embodiment of the present invention will be described with reference to FIG. 37.

Figure 37:
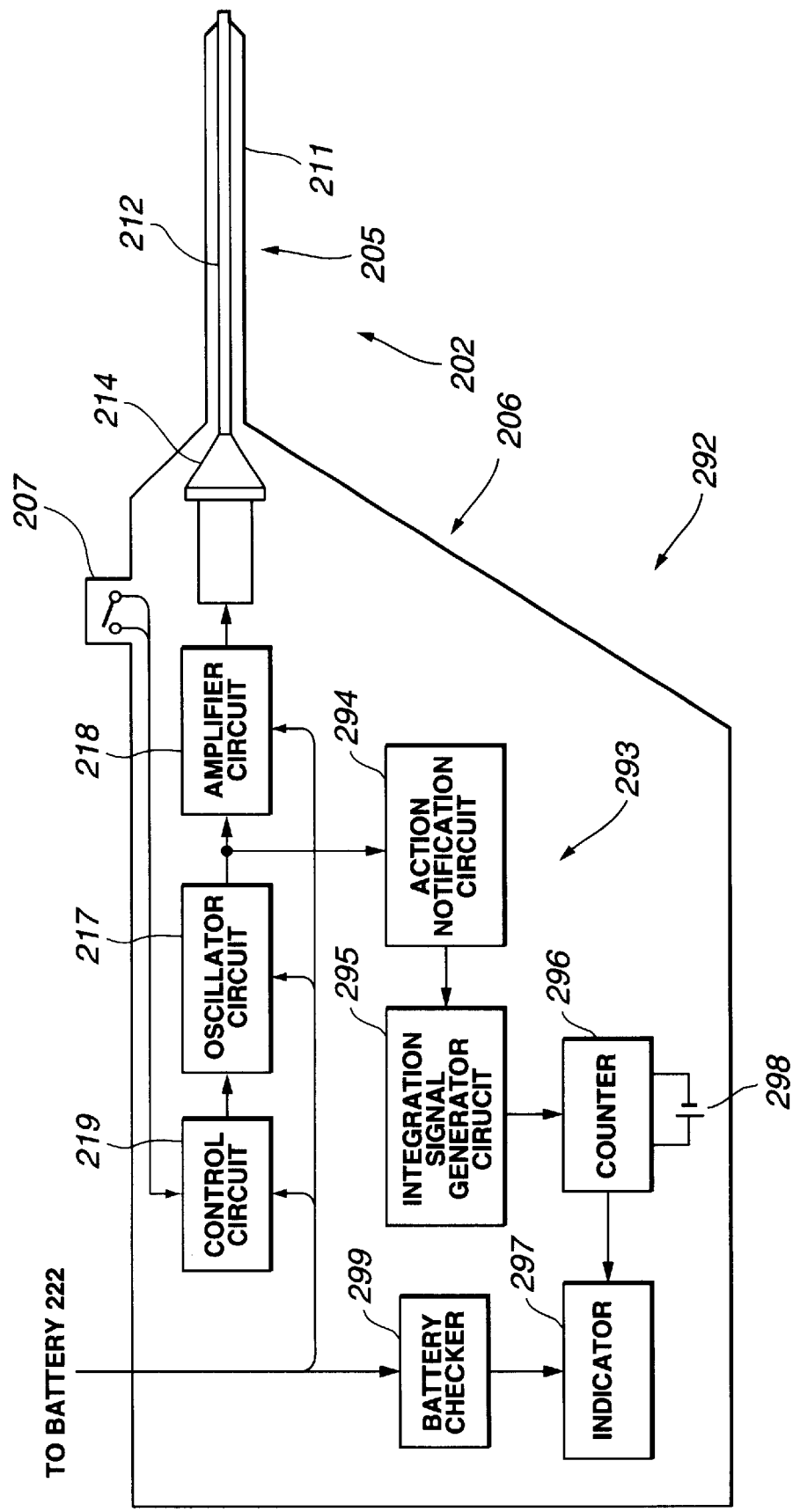
FIG. 37 and FIG. 38 show the eighteenth embodiment of the present invention.

FIG. 37 shows an ultrasonic operation apparatus 292 having the capability of a life meter for judging the service life of a consumable part such as a probe of an ultrasonic cure device. Herein, the ultrasonic operation apparatus 292 has, in addition to the components of the ultrasonic operation apparatus 200 of the eleventh embodiment, a life meter 293 incorporated in, for example, the main body 202. The circuitry described in conjunction with the eleventh embodiment will not be reiterated below. The present embodiment will be described on the assumption that the consumable part is a probe 212.

For activating the probe 212, an oscillator circuit 217 must be activated. The service life of the probe 212 is measured based on an oscillatory signal produced by the oscillator circuit 217. While the probe 212 is in action, that is, while the oscillator circuit 217 is in action, a signal is sent from the oscillator circuit 217 to an action notification circuit 294. The action notification circuit 294 outputs an action notification signal notifying that the probe 212 is in action.

An integration signal generator circuit 295 for generating an integration signal in response to the output signal originates an integration signal (pulses) that varies with time during a time interval corresponding to the use time of the probe 212. The integration signal has pulses thereof counted by a counter 296. Times during which the probe 212 is used are then integrated to provide an integrated time. Thus, an integrating means is realized for calculating an integrated use time of the probe 212.

Furthermore, the use time measured using the counter 296 is indicated with an indicator 297. The counter 296 has a backup battery 298 for backing up the battery 222.

An output of the battery checker 299 for checking the battery 222 is in put to the indicator 297. The result of battery checking is also indicated. These indications, that is, the use time of the probe 212 and the capacity of the battery 222 are indicated alternately or simultaneously.

Figure 38:
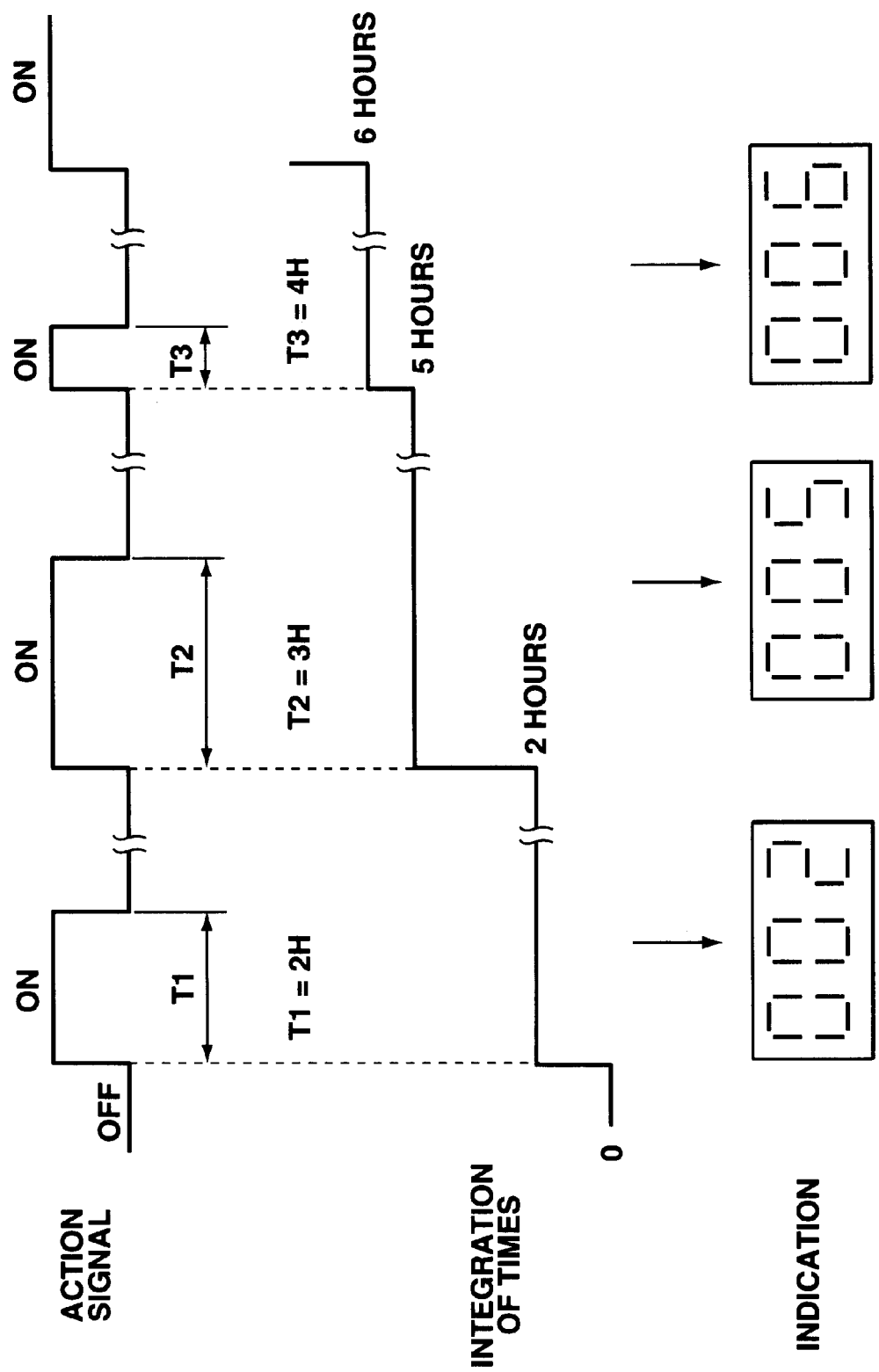

FIG. 38 shows a practical example of ways of integrating times and a practical example of indications.

An example of action signals shown in FIG. 38 is output from the action notification circuit 294. Time T1 denotes, for example, two hours of use, time T2 denotes three hours of use, and time T3 denotes one hour of use. According to an example of ways of integrating times shown in FIG. 38, the output of the counter 296 is two hours, five hours, or six hours which is an integrated time of a previous time and a current time.

The integrated time is indicated with the indicator 297 as shown in an example of indications in FIG. 38. As shown in the example of indications, for example, the integrated time is indicated as 2, 5, or 6 on a three-digit seven-segment display using LEDs. Thus, the integrated use time of the probe 212 is indicated to an operator.

As mentioned above, according to the present embodiment, in addition to the advantages of the eleventh embodiment, the service life of a consumable part such as the probe 212 can be discerned. Moreover, the degree by which electrical energy contained in the battery 222 has been consumed or remains can be determined.

In the present invention, it is apparent that a wide range of different embodiments can be constructed based on the invention without a departure from the spirit and scope of the invention. The present invention will be limited by the appended claims but not be restricted by any specific embodiments.

What is claimed is:

1. An endoscope apparatus capable of alerting a user of exhaustion of a battery, comprising:

an endoscope having a light guide fiber bundle over which illumination light is propagated;

a battery-powered light source having an illumination lamp, freely detachably attached to said endoscope, for supplying illumination light to the incidence end of said light guide fiber bundle on which illumination light falls, and a battery serving as a power supply that causes said illumination lamp to light, wherein at least one of said endoscope and battery-powered light source includes a notifying means for notifying a user of an amount of electrical energy contained in a battery; and said notifying means comprises: an electrical battery energy detecting means for detecting an amount of electrical energy contained in a battery and a capacity-of-battery reporting means for informing a user of the amount of electrical energy contained in the battery;

wherein said capacity-of-battery reporting means is an indication unit for indicating a current amount of electrical energy contained in a battery according to the result of detection performed by said electrical battery energy detecting means; and wherein said indication unit is within a user's field of vision when said user is viewing an image through said endoscope.

2. An endoscope apparatus according to claim 1, wherein said electrical battery energy detecting means detects a voltage given by a dry battery or chargeable battery.

3. An endoscope apparatus according to claim 1, wherein said indication unit is a liquid crystal panel for displaying an indicator that simulates a battery and indicates the capacity of a battery as an index, and said indication unit is included in said battery-powered light source.

4. An endoscope apparatus according to claim 1, wherein said indication unit is a level meter to be lit for reporting the amount of electrical energy contained in said battery, and said indication unit is included in said battery-powered light source.

5. An endoscope apparatus according to claim 1, wherein said indication unit is a lamp to be lit for reporting the amount of electrical energy contained in said battery, and said indication unit is included in at least one of said endoscope and battery-powered light source.

6. An endoscope apparatus according to claim 1, wherein said capacity-of-battery reporting means is a sounding body for emitting a sound so as to report that electrical energy contained in a battery has run low.

7. An endoscope apparatus according to claim 1, wherein said capacity-of-battery reporting means is a vibratory body for making vibratory motions so as to report that electrical energy contained in a battery has run low.

8. An endoscope apparatus according to claim 1, wherein said electrical battery energy detecting means detects a voltage given by a battery with an illumination lamp lit.

9. An endoscope apparatus according to claim 1, wherein when a user manipulates a switch for reporting, said electrical battery energy detecting means reports an amount of electrical energy contained in a battery to the user via said indication unit.

10. An endoscope apparatus according to claim 1, wherein said electrical battery energy detecting means reports an amount of electrical energy contained in a battery to a user via said indication unit irrespective of whether said illumination lamp is on or off.

11. An endoscope apparatus according to claim 1, wherein said electrical battery energy detecting means performs intermittent reporting and continuous reporting in predetermined combination.

12. An endoscope apparatus according to claim 1, wherein said electrical battery energy detecting means performs intermittent reporting alone.

13. An endoscope apparatus according to claim 1, wherein said battery is a chargeable battery, said electrical battery energy detecting means reports at least a charge time at which said chargeable battery should be charged.

14. An endoscope apparatus capable of alerting a user of exhaustion of a battery, comprising:

an endoscope having a light guide fiber bundle over which illumination light is propagated;

a battery-powered light source having an illumination lamp, freely detachably attached to said endoscope, for supplying illumination light to the incidence end of said light guide fiber bundle on which illumination light falls, and a battery serving as a power supply that causes said illumination lamp to light, wherein at least one of said endoscope and battery-powered light source includes a notifying means for notifying a user of an amount of electrical energy contained in a battery; said notifying means comprises: an electrical battery energy detecting means for detecting an amount of electrical energy contained in a battery and a capacity-of-battery reporting means for informing a user of the amount of electrical energy contained in the battery;

wherein said capacity-of-battery reporting means is an indication unit for indicating a current amount of electrical energy contained in a battery according to the result of detection performed by said electrical battery energy detecting means; and wherein said indication unit is included in an eyepiece unit of said endoscope.

15. An endoscope apparatus capable of alerting a user of exhaustion of a battery, comprising:

an endoscope having a light guide fiber bundle over which illumination light is propagated;

a battery-powered light source having an illumination lamp, freely detachably attached to said endoscope, for supplying illumination light to the incidence end of said light guide fiber bundle on which illumination light falls, and a battery serving as a power supply that causes said illumination lamp to light, wherein at least one of said endoscope and battery-powered light source includes a notifying means for notifying a user of an amount of electrical energy contained in a battery; and said notifying means comprises: an electrical battery energy detecting means for detecting an amount of electrical energy contained in a battery and a capacity-of-battery reporting means for informing a user of the amount of electrical energy contained in the battery;

wherein said capacity-of-battery reporting means is an indication unit for indicating a current amount of electrical energy contained in a battery according to the result of detection performed by said electrical battery energy detecting means;

wherein said indication unit is a liquid crystal panel for displaying an indicator that simulates a battery and indicates the capacity of a battery as an index, and said indication unit is included in said battery-powered light source; and wherein said liquid crystal panel displays an indicator for reporting the amount of electrical energy contained in said battery and also displays an endoscopic image.

16. An endoscope apparatus according to claim 15, wherein said reporting means is placed on a plane parallel to a view image provided by an eyepiece unit.

17. An endoscope apparatus capable of alerting a user of exhaustion of a battery, comprising:

an endoscope having a light guide fiber bundle over which illumination light is propagated;

a battery-powered light source having an illumination lamp, freely detachably attached to said endoscope, for supplying illumination light to the incidence end of said light guide fiber bundle on which illumination light falls, and a battery serving as a power supply that causes said illumination lamp to light, wherein at least one of said endoscope and battery-powered light source includes a notifying means for notifying a user of an amount of electrical energy contained in a battery; and said notifying means comprises: an electrical battery energy detecting means for detecting an amount of electrical energy contained in a battery and a capacity-of-battery reporting means for informing a user of the amount of electrical energy contained in the battery; and wherein said electrical battery energy detecting means further comprises a memory circuit for integrating lighting times during which said illumination lamp is lit and storing an integrated time.

18. An endoscope apparatus according to claim 17, wherein said memory circuit includes a recording and holding unit that is conducting all the time and has the ability to record and hold data.

19. An endoscope apparatus according to claim 18, wherein said recording and holding unit is a nonvolatile memory.

20. An endoscope apparatus according to claim 17, wherein said electrical battery energy detecting means further comprises an arithmetic circuit for calculating a remaining usable time of said battery according to an integrated usable time output from said memory circuit and a voltage value detected by said detecting means.

* * * * *